(12) United States Patent
Gronseth et al.

(10) Patent No.: US 10,201,327 B2
(45) Date of Patent: *Feb. 12, 2019

(54) ORGANIC SPECIMEN FEATURE IDENTIFICATION IN ULTRASOUND DATA

(71) Applicants: Cliff A. Gronseth, Boulder, CO (US); John E. Tobey, Louisville, CO (US)

(72) Inventors: Cliff A. Gronseth, Boulder, CO (US); John E. Tobey, Louisville, CO (US)

( * ) Notice: Subject to any disclaimer, the term of this patent is extended or adjusted under 35 U.S.C. 154(b) by 105 days.

This patent is subject to a terminal disclaimer.

(21) Appl. No.: 15/143,628

(22) Filed: May 1, 2016

(65) Prior Publication Data

US 2016/0270761 A1    Sep. 22, 2016

Related U.S. Application Data

(63) Continuation-in-part of application No. 14/322,640, filed on Jul. 2, 2014, now Pat. No. 9,357,979, which
(Continued)

(51) Int. Cl.
*A61B 8/00* (2006.01)
*A61B 8/08* (2006.01)
*A61B 8/13* (2006.01)

(52) U.S. Cl.
CPC .......... *A61B 8/4245* (2013.01); *A61B 8/0875* (2013.01); *A61B 8/4209* (2013.01);
(Continued)

(58) Field of Classification Search
CPC ... A61B 8/4245; A61B 8/0875; A61B 8/4209; A61B 8/4218; A61B 8/463; A61B 8/483;
(Continued)

(56) References Cited

U.S. PATENT DOCUMENTS

| 8,805,627 B2* | 8/2014 | Gronseth ............. A61B 8/4218 382/128 |
| 2007/0010743 A1* | 1/2007 | Arai ........................ A61B 8/13 600/443 |

(Continued)

*Primary Examiner* — Matthew G Marini
(74) *Attorney, Agent, or Firm* — Tobey & Associates, LLC; Morley C. Tobey, Jr.

(57) ABSTRACT

A system, method, and non-transitory computer-readable medium. The system includes a processor configured to receive reference ultrasound data from ultrasound reflected waves received from specimen features in an organic specimen resultant from reference ultrasound incident waves transmitted into the organic specimen, wherein positional awareness of each ultrasound reflected wave relative to the organic specimen is maintained; to identify a reference propagation region in the organic specimen into which the reference ultrasound incident waves were transmitted into the organic specimen and a corresponding reference model image region in anatomic model data corresponding to at least part of the organic specimen; and to receive additional ultrasound data from ultrasound reflected waves received from specimen features in the organic specimen resultant from additional ultrasound incident waves transmitted into the organic specimen, wherein positional awareness is maintained between the reference propagation region and a propagation region of the additional ultrasound data.

45 Claims, 20 Drawing Sheets

Related U.S. Application Data is a continuation of application No. 13/135,350, filed on Jul. 1, 2011, now Pat. No. 8,805,627.

(52) U.S. Cl.
CPC ............ *A61B 8/4218* (2013.01); *A61B 8/463* (2013.01); *A61B 8/464* (2013.01); *A61B 8/483* (2013.01); *A61B 8/5223* (2013.01); *A61B 8/5238* (2013.01); *A61B 8/0841* (2013.01); *A61B 8/13* (2013.01); *A61B 8/4263* (2013.01); *A61B 8/466* (2013.01); *A61B 8/5215* (2013.01); *Y10S 128/903* (2013.01); *Y10S 128/904* (2013.01)

(58) Field of Classification Search
CPC ... A61B 8/5223; A61B 8/5238; A61B 8/0841; A61B 8/13; A61B 8/4263; A61B 8/466; Y10S 128/903; Y10S 128/904
See application file for complete search history.

(56) References Cited

U.S. PATENT DOCUMENTS

| | | | |
|---|---|---|---|
| 2008/0275339 A1* | 11/2008 | Thiemann | A61B 8/0833 600/437 |
| 2009/0036775 A1* | 2/2009 | Ikuma | A61B 8/12 600/443 |
| 2011/0201935 A1* | 8/2011 | Collet-Billon | A61B 8/0833 600/443 |

\* cited by examiner

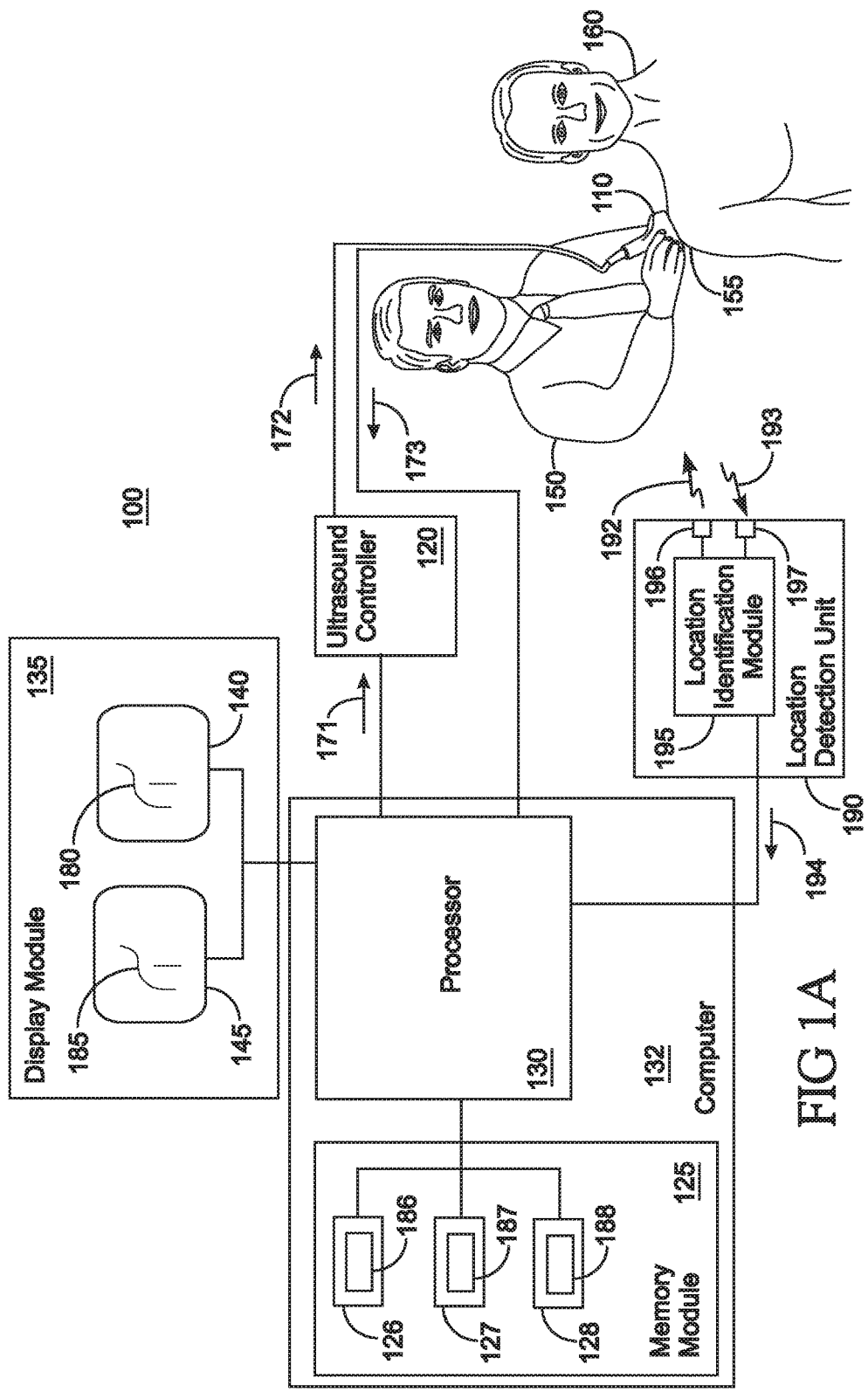

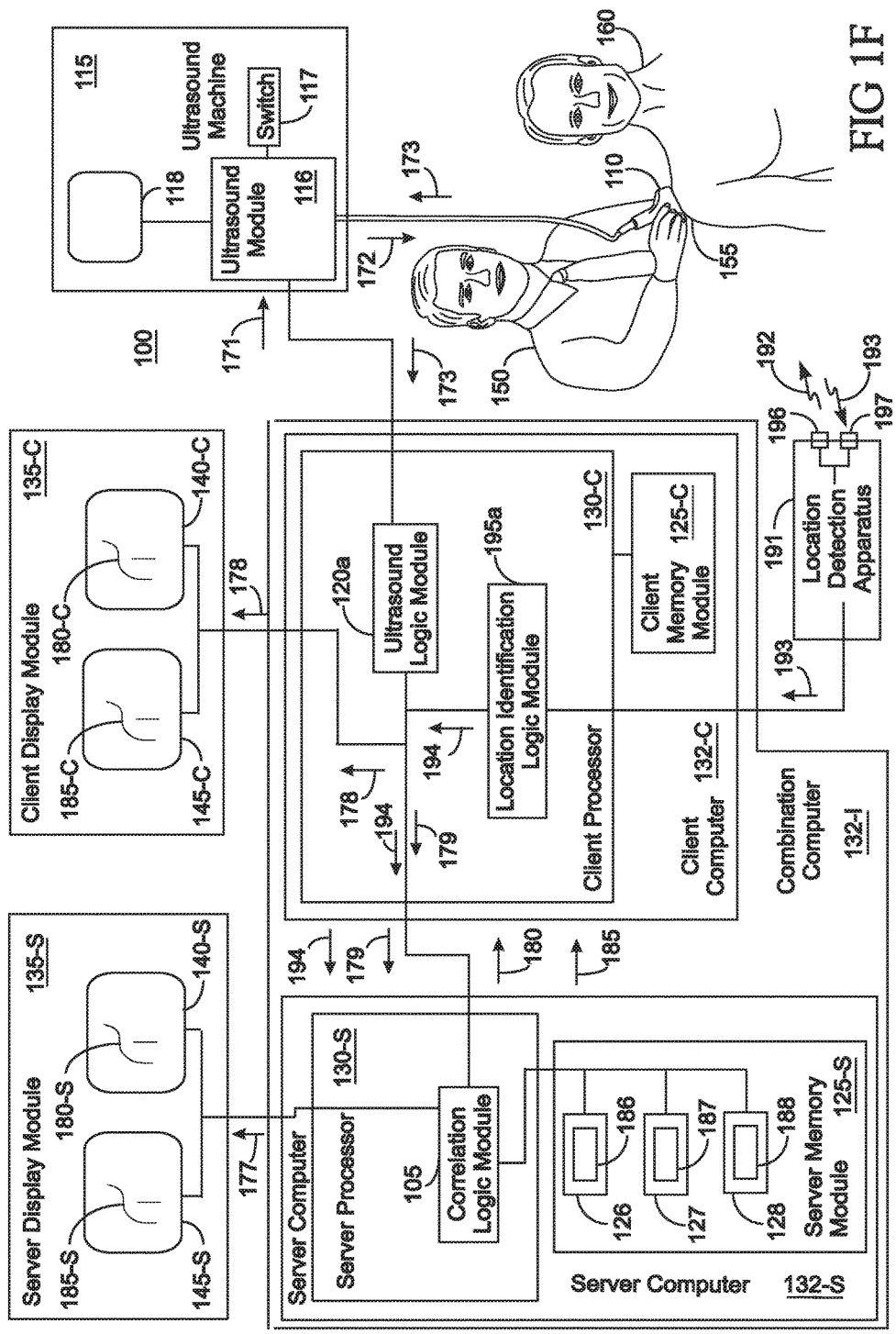

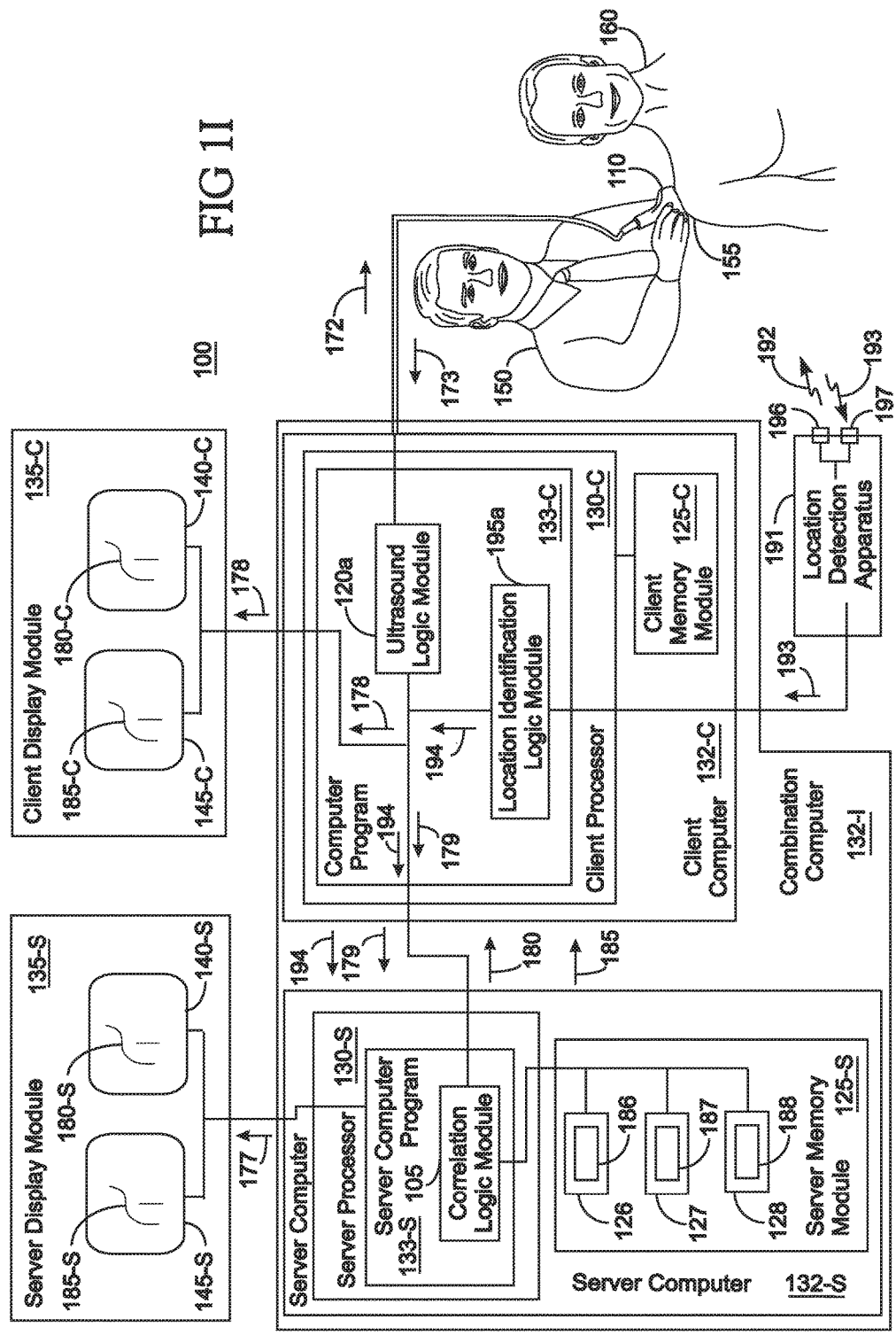

ORGANIC SPECIMEN FEATURE IDENTIFICATION IN ULTRASOUND DATA

CROSS-REFERENCE TO RELATED APPLICATIONS

This application claims the priority of U.S. patent application Ser. No. 13/135,350, now issued as U.S. Pat. No. 8,805,627, by Cliff A. Gronseth and John E. Tobey, filed 1 Jul. 2011, and entitled "METHOD AND SYSTEM FOR ORGANIC SPECIMEN FEATURE IDENTIFICATION IN ULTRASOUND IMAGE" of which the entire contents are incorporated herein by reference and claims the priority of U.S. patent application Ser. No. 14/322,640, now issued as U.S. Pat. No. 9,357,979, by Cliff A. Gronseth and John E. Tobey, filed 2 Jul. 2014, and entitled "METHOD AND SYSTEM FOR ORGANIC SPECIMEN FEATURE IDENTIFICATION IN ULTRASOUND IMAGE" of which the entire contents are incorporated herein by reference.

BACKGROUND

Ultrasonic waves are used in various cleaning applications, in medical diagnostic and therapeutic applications, and for a number of research and investigative purposes. Ultrasound has become a widely used, medical diagnostic tool and is generally considered to be safe as well as non-invasive. One of the more well known medical applications is in the creation of visual images of fetuses in the human womb for diagnostic purposes. In other medical areas, however, ultrasound is now used as a diagnostic tool in the creation of visual images of muscles, tendons, and various internal organs. In such applications, the size, structure, and pathological lesions of bodily soft tissues can be captured via real time tomographic images.

Compared with other diagnostic technologies, such as magnetic resonance imaging (MRI) and computed tomography (CT), ultrasound machines are relatively inexpensive and portable. While X-rays are useful for medical purposes in obtaining images of bones, ultrasonic waves find their medical applications in the creation of soft tissue images. An advantage of ultrasonic waves is that they do not have the negative biological effects associated with X-rays or with other techniques involving radioactive materials.

SUMMARY

In a first representative embodiment, a system is disclosed. The system comprises an ultrasound transducer configured for transmitting ultrasound incident waves into selected regions of an organic specimen, detecting resultant ultrasound reflected waves from specimen features of the organic specimen, and transferring ultrasound data in the resultant ultrasound reflected waves for each of multiple selected ultrasound incident waves to a processor; a location detection unit configured for detecting locations of the ultrasound transducer and the organic specimen and for transferring that location data to the processor; a memory module configured for storing anatomic model data for at least part of the organic specimen; the processor configured for identifying the region associated with selected ultrasound data using location data and one or more sets of ultrasound data resultant from reflections of recognized specimen features, creating an ultrasound image from the selected ultrasound data, obtaining model extracted data from the anatomic model data corresponding to that of the selected ultrasound data region, creating a model image from that model extracted data, and transferring the ultrasound image and the model image to a display module; and the display module configured for displaying the ultrasound image and the model image.

In a second representative embodiment, a method is disclosed. The method comprises specifying a reference model image region in model extracted data obtained from anatomic model data of at least part of an organic specimen; transmitting ultrasound incident waves into the organic specimen and receiving thereby ultrasound data from ultrasound reflected waves from specimen features in the organic specimen, wherein positional awareness of each ultrasound reflected wave relative to the organic specimen is maintained; identifying a reference propagation region corresponding to the reference model image region from paired recognized specimen features in the ultrasound data and in the model extracted data; transmitting at least one subsequent ultrasound incident wave into the organic specimen and receiving thereby subsequent ultrasound data from ultrasound reflected waves from one or more specimen features, wherein positional awareness is maintained between the reference propagation region and the propagation region of the subsequent ultrasound data; and for the subsequent ultrasound data, creating an ultrasound image, creating a model image for a model image region from the anatomic model data corresponding to the propagation region of the subsequent ultrasound data, and displaying the ultrasound image and the model image on a display module.

In an optional aspect of the second representative embodiment, the method further comprises identifying at least one specimen feature on the ultrasound image from a corresponding model feature on the model image.

In a third representative embodiment, a means for identification of an organic specimen feature in an ultrasound image is disclosed. The means comprises an ultrasound means for transmitting ultrasound incident waves into selected regions of an organic specimen, detecting resultant ultrasound reflected waves from specimen features of the organic specimen, and transferring ultrasound data in the resultant ultrasound reflected waves for each of multiple selected ultrasound incident waves to a processor means; a location detection means for detecting locations of the ultrasound means and the organic specimen and for transferring that location data to the processor means; a memory means for storing anatomic model data for at least part of the organic specimen; the processor means for identifying a region of the organic specimen associated with selected ultrasound data using location data and one or more sets of ultrasound data resultant from reflections of recognized specimen features, creating an ultrasound image from the selected ultrasound data, obtaining model extracted data from the anatomic model data corresponding to that of the selected ultrasound data region, creating a model image from the model extracted data, and transferring the ultrasound image and the model image to a display means; and the display means configured for displaying the ultrasound image and the model image.

In a fourth representative embodiment, a computer program product stored on a non-transitory computer readable storage medium for carrying out a method when executed on a computer is disclosed. The method comprises specifying a reference model image region in model extracted data obtained from anatomic model data of at least part of an organic specimen; instructing an ultrasound transducer to transmit ultrasound incident waves into the organic specimen and receiving thereby ultrasound data from ultrasound reflected waves from specimen features in the organic specimen, wherein positional awareness of each ultrasound reflected wave relative to the organic specimen is maintained; identifying a reference propagation region corresponding to the reference model image region from paired recognized specimen features in the ultrasound data and in the model extracted data; instructing an ultrasound transducer to transmit at least one subsequent ultrasound incident wave into the organic specimen and receiving thereby subsequent ultrasound data from ultrasound reflected waves from one or more specimen features, wherein positional awareness is maintained between the reference propagation region and the propagation region of the subsequent ultrasound data; and for the subsequent ultrasound data, creating an ultrasound image, creating a model image for a model image region from the anatomic model data corresponding to the propagation region of the subsequent ultrasound data, and instructing a display module to display the ultrasound image and the model image.

In a fifth representative embodiment, a non-transitory computer-readable medium having computer-executable instructions for causing a computer comprising a processor and associated memory to carry out a method is disclosed. The method comprises specifying a reference model image region in model extracted data obtained from anatomic model data of at least part of an organic specimen; instructing an ultrasound transducer to transmit ultrasound incident waves into the organic specimen and receiving thereby ultrasound data from ultrasound reflected waves from specimen features in the organic specimen, wherein positional awareness of each ultrasound reflected wave relative to the organic specimen is maintained; identifying a reference propagation region corresponding to the reference model image region from paired recognized specimen features in the ultrasound data and in the model extracted data; instructing an ultrasound transducer to transmit at least one subsequent ultrasound incident wave into the organic specimen and receiving thereby subsequent ultrasound data from ultrasound reflected waves from one or more specimen features, wherein positional awareness is maintained between the reference propagation region and the propagation region of the subsequent ultrasound data; and for the subsequent ultrasound data, creating an ultrasound image, creating a model image for a model image region from the anatomic model data corresponding to the propagation region of the subsequent ultrasound data, and instructing a display module to display the ultrasound image and the model image.

BRIEF DESCRIPTION OF THE DRAWINGS

The accompanying drawings provide visual representations which will be used to more fully describe various representative embodiments disclosed herein. They can be used by those skilled in the art to better understand the representative embodiments. In these drawings, like reference numerals identify corresponding elements.

FIG. 1A is a block diagram of a system for identification of organic specimen features in ultrasound images as described in various representative embodiments.

FIG. 1F is a block diagram of a system for the identification of corresponding features in ultrasound data obtained from an organic specimen and in model data for that organic specimen as described in various representative embodiments.

FIG. 1I is a block diagram of yet another system for the identification of corresponding features in ultrasound data obtained from an organic specimen and in model data for that organic specimen as described in various representative embodiments.

DETAILED DESCRIPTION

Figure 1B:
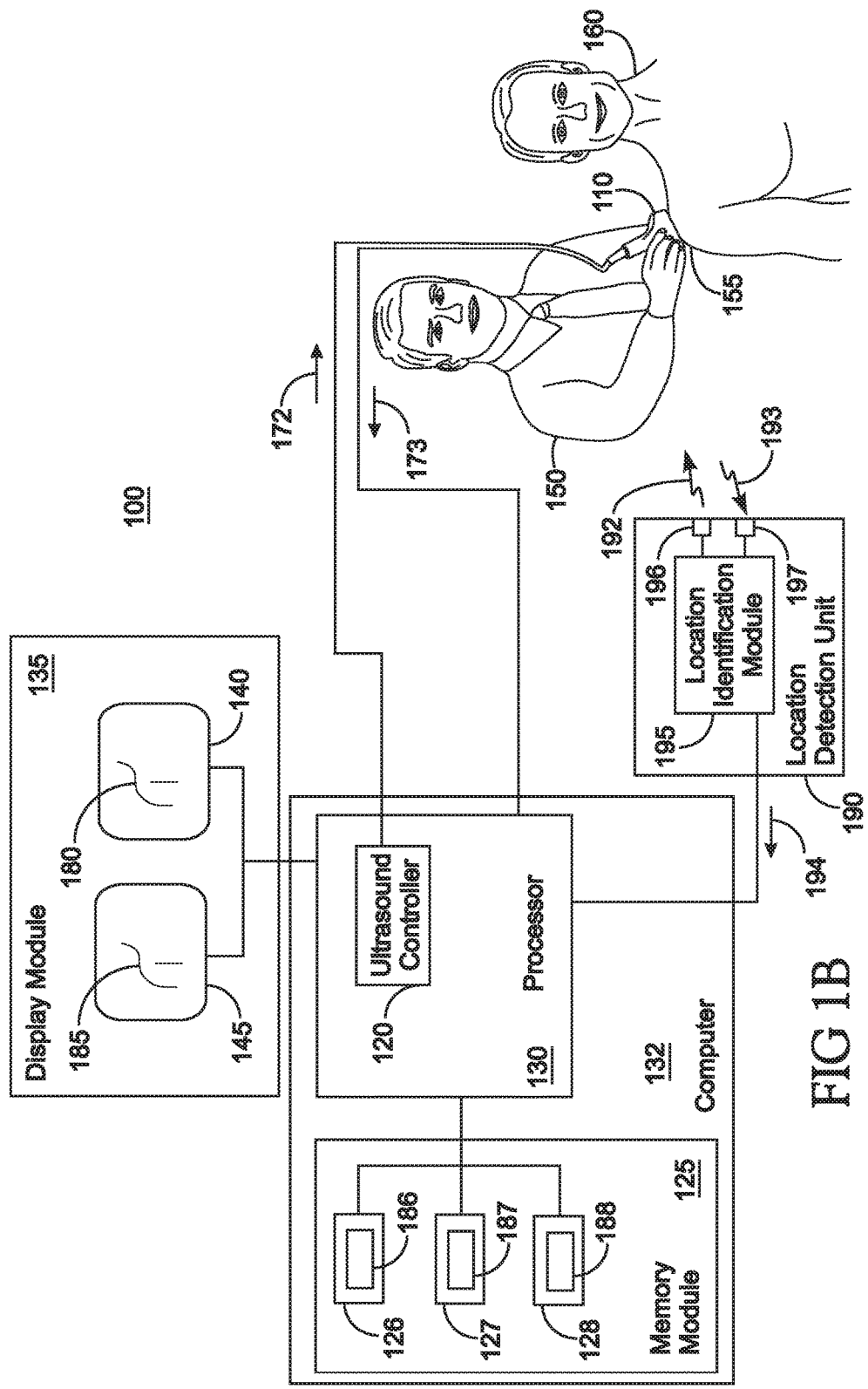
FIG. 1B is a block diagram of another system for identification of organic specimen features in ultrasound images as described in various representative embodiments.

Novel techniques are disclosed herein of methods and systems for the identification of organic features in ultrasound images of organic specimens as shown in the drawings for purposes of illustration. An organic specimen is any living or deceased organism or a portion of a living or deceased organism. In particular, the organic specimen could be a human, another animal, a plant, or a portion of a human, another animal, or a plant. The human could be a baby, an infant, a child, an adolescent, a teenager, or an adult.

Ultrasound has been used to monitor fetus development in the womb and more recently for diagnosis in musculoskeletal applications. Musculoskeletal applications include the diagnosis of muscle tears, tendon tears such as rotator cuff tears, nerve problems, blood clots in the vascular system, and the like. Musculoskeletal ultrasound images differ from those obtained in monitoring fetus development in the womb in that the musculoskeletal ultrasound transducer transmits its signal in a straight line rather than a curve. As such, a straight tendon will be displayed as a straight line on the ultrasound monitor. Such ultrasound machines are being used more and more in outpatient settings. MRI, as well as ultrasound, can be used to create images of soft, internal body tissues, but MRIs are expensive. Nuclear methods can also be used but are less desirable than ultrasound as they expose the body to radiation. Another advantage of ultrasound is that it can be used to create dynamic pictures rather than the static pictures of MRI. Ultrasound diagnostic systems provide immediate images, are portable, are safe, and are economical.

However, current systems require extensive training to develop the skills necessary for interpreting ultrasound images. Even after extensive training, inaccurate diagnoses are not uncommon, and results are often inconsistent from one operator to another. Correctly identifying a patient's internal features in an ultrasound image has been strongly dependent upon the skill of the operator that is interpreting the image. The greatest barrier to the use of ultrasound is that it must be practiced over and over again which is time consuming and expensive. The operator must be able to correctly identify the tissue displayed in an ultrasound image which means that he/she must also know anatomy in great detail as there are a large number of different parts of the human anatomy that can be detected by ultrasound. The number of operators that have had an acceptable level of this skill has been very limited, and the cost of obtaining this skill has been expensive.

Conversely, the representative embodiments disclosed herein provide systems and methods that can significantly reduce operator training time and thereby training expense, can reduce the incidence of an inaccurate diagnosis by the correct identification of tissues, and can reduce the variation from operator to operator in a diagnosis.

While the present invention is susceptible to embodiment in many different forms, there is shown in the drawings and will herein be described in detail one or more specific embodiments, with the understanding that the present disclosure is to be considered as exemplary of the principles of the invention and is not intended to limit the invention to the specific embodiments shown and described. In the following description and in the several figures of the drawings, like reference numerals are used to describe the same, similar, or corresponding parts in the several views of the drawings.

In representative embodiments, an ultrasound image obtained from an organic specimen under study is correlated with data that represents or models all or part of that organic specimen. By first identifying certain features and anatomic patterns in the organic specimen that are relatively easy to identify and correlating that information with data from the model of the organic specimen, a reference position of an ultrasound transducer with respect to the organic specimen can be identified. Then while maintaining knowledge of any subsequent movement of the ultrasound transducer and/or any subsequent movement of the organic specimen relative to the reference locations of the ultrasound transducer and the organic specimen, subsequent ultrasound images of the organic specimen can be correlated with images created from the model. This correlation enables an operator to relatively easily identify features in the organic specimen on the ultrasound image. A software program could be used to automatically identify such features. To facilitate identification of features of the organic specimen, the ultrasound and model images can be displayed simultaneously either on two separate displays or together on a single display. In alternative embodiments, the two images could be overlaid, and certain features in one or the other images could be differentially colored, displayed with dashes, dots, or otherwise differentiated lines and areas, labeled and/or otherwise appropriately identified. Also, one or the other images could be faded in and out. A computer program could provide texted or auditory identification of a specific tissue upon request. In addition, the operator could preselect particular features of interest to be emphasized when found in an ultrasound image. Such emphasis can also be added by, for example, the addition of a preselected color to the feature of interest, a flashing indicator, displayed with dashes, dots, or otherwise differentiated lines and areas, labels and/or other appropriate means. Movement of the ultrasound transducer could be programmatically controlled so as to locate preselected features on the organic specimen with little or no operator assistance.

As the ultrasound transducer is moved, the location of the ultrasound transducer relative to its identified, reference location can be maintained by a mechanical fixture attached to the ultrasound transducer, by the detection of targets placed on the ultrasound transducer using mechanical, infrared, optical, radio frequency, inertial means, or by any other acceptable means. The location of the organic specimen relative to the identified, reference location of the ultrasound transducer can be maintained by holding the organic specimen immobilized, by a mechanical fixture attached to a non-moving surface and to the organic specimen, or by the detection of targets placed on the organic specimen using, mechanical coupling, infrared, optical, radio frequency, inertial means, or by any other acceptable means.

The Visible Human Project® (VHP) is an effort to create a detailed data set from cross-sectional photographs of the human body. The Visible Human Project® is a registered trademark of the National Library of Medicine. To obtain the data, successive layers of a male and a female cadaver were removed by grinding away the top surface at regular intervals. Each of the revealed planar surfaces was photographed and stored electronically. Image data for each pixel in the two-dimensional photographs are stored in digital format along with their associated three-dimensional coordinates. Pixel image and associated coordinate data can be used to create two-dimensional and three-dimensional images of a representative human body (male or female) at diverse selected depths and angular orientations.

In representative embodiments, anatomic model data which could be, for example, the VHP data are used in combination with ultrasound data and a three-dimensional location detection device to create correlated model and ultrasound images in a human patient as well as other organic entities. These correlated images can be used to facilitate the identification of specific features in the ultrasound images of the human patient or other organic specimen. A location detection unit could use a set of targets coupled to the organic specimen and another set of targets coupled to the ultrasound transducer to acquire the location and orientation of the ultrasound transducer relative to the organic specimen. These targets could be identified and located by mechanical coupling means, optical, infrared, radio frequency, inertial means, or other appropriate techniques or by a combination of such techniques. Once the reference location of the ultrasound transducer relative to the patient (the organic specimen) is set, the location detection unit monitors any subsequent motion of the ultrasound transducer and/or the patient, identifies the related subsequent location of the ultrasound transducer and patient, and identifies, thereby, the location and orientation of the ultrasound image and the associated model image. A split screen, dual screen, or other appropriate display module can be used to view the ultrasound and model images obtained. By correlating the ultrasound and model images and by identifying features on the model image by some means which could be, for example, by the use of tags, features on the ultrasound image can be readily identified by an operator. Using such embodiments, it is no longer necessary for the operator to receive the extensive training that has previously been required. Previously several years of expensive training typically have been needed for an operator to attain the needed skill level.

Due to the large amount of data that can be associated with any given model, it may be advantageous to divide the model into different specific areas of interest such as, for example, a shoulder, an elbow, a wrist, a hip, or other specific body part. Once the operator identifies a known feature of the patient, which could be, for example, the small notch in the bones of a shoulder in which the bicep tendon passes through or other readily identifiable feature, the operator could push a button or click a mouse button to select that feature as one used for setting a plane of reference. Once the reference frame is selected, the operator could select a feature on the ultrasound image by a mouse click or other means and a program could then identify that feature and notify the operator of its identity. In representative embodiments, systems and methods disclosed herein could be used as a diagnostic tool and/or as a teaching tool.

Pathology in the anatomic model data could be digitally repaired so that the model is in pristine condition prior to its use with ultrasound images. The human anatomic model data might have, for example, a rotator cuff tear or other damage. Repairing this tear in the anatomic model data would facilitate detecting similar damage in the patient. Based on the distances between features in the ultrasound image used to set the reference location of the ultrasound transducer relative to the patient (the organic specimen), the model image can be appropriately scaled to match the size of the patient. Alternatively, the anatomic model data could have previously been scaled to certain preset representative patient sizes such as, for example, small, medium, and large and adjusted to known anatomic variants.

While the representative embodiments disclosed herein are discussed in terms of static two-dimensional model and ultrasound images, the representative embodiments can also be implemented using time varying two-dimensional model and ultrasound images, static three-dimensional model and ultrasound images, and time varying three-dimensional model and ultrasound images. As appropriate, these images can be displayed on a two-dimensional display system as static or time varying two-dimensional images and on a three-dimensional display system as static or time varying three-dimensional images.

The descriptor "image" is used generally herein to describe a data set or data stream which is representative of at least a portion of a model of an organic specimen or as found in or from data of ultrasound data obtained from the organic specimen. The descriptor "image" may be, but is not limited to, a data set representative of at least a part of a file or data stream of the organic specimen or model thereof which is intended for visual display. Further, the descriptor "image" otherwise may be a data set representative of at least a part of a file or data stream of the organic specimen or model thereof which is not intended for visual display.

FIG. 1A is a block diagram of a system 100 for identification of organic specimen 160 features in ultrasound images 180 as described in various representative embodiments. An ultrasound image 180 is also referred to herein as ultrasound image data 180. The system 100 comprises an ultrasound transducer 110, an ultrasound controller 120, a display module 135, a location detection unit 190, and a computer 132. The computer 132 comprises a memory module 125 and a processor 130. In FIG. 1A, the display module 135 comprises an ultrasound display 140 also referred to herein as a first display 140 and a model display 145 also referred to herein as a second display 145. The memory module 125 comprises an anatomic model memory 126, an ultrasound memory 127, and an extracted model memory 128. The location detection unit 190 comprises an emitter device 196, a receptor device 197, and a location identification module 195.

The ultrasound transducer 110 is separately coupled to the ultrasound controller 120 and to the processor 130. The processor 130 is also coupled to the location detection unit 190 which transfers information regarding the relative locations of the ultrasound transducer 110 and the organic specimen 160 via location data 194 to the processor 130, to the memory module 125 within which the processor 130 is coupled to the anatomic model memory 126, the ultrasound memory 127, and the extracted model memory 128, to the display module 135 within which the processor 130 is coupled to the ultrasound display 140 and the model display 145, and to the ultrasound controller 120. Coupling between the various components of the system 100 could be via electronic cables, optical fibers, pairs of radio frequencies or infrared transmitter/receivers, or other appropriate means for transmitting or transferring signals.

The ultrasound memory 127 is configured to store sets of ultrasound data 187 obtained from the ultrasound transducer 110. The anatomic model memory 126 is configured to store anatomic model data 186 which is a model of and representative of at least part 155 of an organic specimen 160. The extracted model memory 128 is configured to store sets of model extracted data 188. In representative embodiments, a set of model extracted data 188 can be obtained from the anatomic model data 186 for each set of ultrasound data 187 and can be associated with each set of ultrasound data 187. Each associated set of ultrasound data 187 and model extracted data 188 can be used to create associated ultrasound and model images 180,185 wherein the model image 185 is a model of the region from which the ultrasound image 180 is obtained. A model image 185 is also referred to herein as model image data 185. The terms ultrasound image 180 and ultrasound image data 180 generally refer to data sets or data streams which are representative of at least a portion of an organic specimen 160. They may or may not be intended for or in a format for visual presentation on a display. The terms model image 185 and model image data 185 generally refer to data sets or data streams which are representative of at least a portion of a model of an organic specimen 160. They may or may not be intended for or in a format for visual presentation on a display. The processor 130 is configured to obtain the appropriate set of model extracted data 188 and correlate it with its associated set of ultrasound data 187. In an alternate representative embodiment, the model image 185 can be created from the set of model extracted data 188 without storage of the model extracted data 188. And in another alternate representative embodiment, the set of ultrasound data 187 and the set of model extracted data 188 are stored jointly in a single memory which could be the ultrasound memory 127. The ultrasound image 180 can be displayed on the ultrasound display 140, and concurrently the model image 185 associated with the ultrasound image 180 can be displayed on the model display 145.

The location identification module 195 is configured to instruct the emitter device 196 to transmit location interrogation signals 192 to transducer targets 230 (see FIG. 2 and discussion therewith) on the ultrasound transducer 110 and to specimen targets 240 (see FIG. 2 and discussion therewith) on an organic specimen 160 which could be a patient 160. Upon reception of the location interrogation signals 192 by the transducer targets 230 and the specimen targets 240, the transducer targets 230 and the specimen targets 240 separately respond with location information signals 193 which can be received by the receptor device 197. Information from the location information signals 193 received by the receptor device 197 is transferred from the receptor device 197 to the location identification module 195. The location identification module 195 is further configured to extract location information for the transducer targets 230 and the specimen targets 240 from the information in the location information signals 193 and/or from the location interrogation signals 192. The extracted location information for the transducer targets 230 and the specimen targets 240 is transferred to the processor 130 as location data 194. The location data 194 can be used by the processor 130 to associate a specific set of ultrasound data 187 with the relative locations and orientations of the ultrasound transducer 110 and the organic specimen 160 for which that set of ultrasound data 187 was obtained. The location data 194 can also be used by the processor 130 to obtain a set of model extracted data 188 from the anatomic model data 186 for the region from which the set of ultrasound data 187 is obtained. This set of model extracted data 188 is thereby associated with that set of ultrasound data 187.

In representative embodiments, an operator 150 holds the ultrasound transducer 110 against, for example, a shoulder 155 of a patient 160. The patient 160 shown in FIG. 1A could more generally be any organic specimen 160 and more particularly could be a person 160, a baby 160, another animal 160, a plant 160 or the like. However, the term organic specimen 160 as used herein more generally means any living or deceased organism or any portion of a living or deceased organism. In particular, the organic specimen could be a human, another animal, a plant, a portion of a human, a portion of another animal, or a portion of a plant. The shoulder 155 shown in FIG. 1A could more generally be a part 155 of any organic specimen 160. The initiation signal 171, the activation signal 172 and reflected data signal 173 will be more completely described with the description of FIG. 2. The anatomic model data 186 stored in the memory module 125 could be anatomic model data 186 of at least part 155 of the organic specimen 160. In representative embodiments, the anatomic model data 186 could be obtained, for example, from the Visible Human Project® (VHP) or other appropriate data which can be used, for example, to create two-dimensional model images 185 of a representative human body (male or female) at diverse selected depths and angular orientations. The VHP data and other model data sources could be used to create static two-dimensional, static three-dimensional, time varying two-dimensional, and/or time varying three-dimensional model images 185. Various components of FIG. 1A will be more completely described with the description of subsequent figures.

While the representative embodiments disclosed herein are discussed in terms of static two-dimensional model and ultrasound images 185,180, the representative embodiments can also be implemented using time varying two-dimensional model and ultrasound images 185,180, static three-dimensional model and ultrasound images 185,180, and time varying three-dimensional model and ultrasound images 185,180. As appropriate, these images can be displayed, for example, on a two-dimensional display system as static or time varying two-dimensional images and on a three-dimensional display system as static or time varying three-dimensional images.

FIG. 1B is a block diagram of another system 100 for identification of organic specimen 160 features in ultrasound images 180 as described in various representative embodiments. The system 100 of FIG. 1B differs from that of FIG. 1A by the inclusion of the functions of the ultrasound controller 120 in the processor 130. In this embodiment, the processor 130 comprises the ultrasound controller 120 which creates the activation signal 172 directly and then transfers the activation signal 172 to the ultrasound transducer 110. Again, the activation signal 172 and the reflected data signal 173 will be more completely described with the description of FIG. 2, and various other components of FIG. 1B will be more completely described with the description of subsequent figures.

Figure 1C:
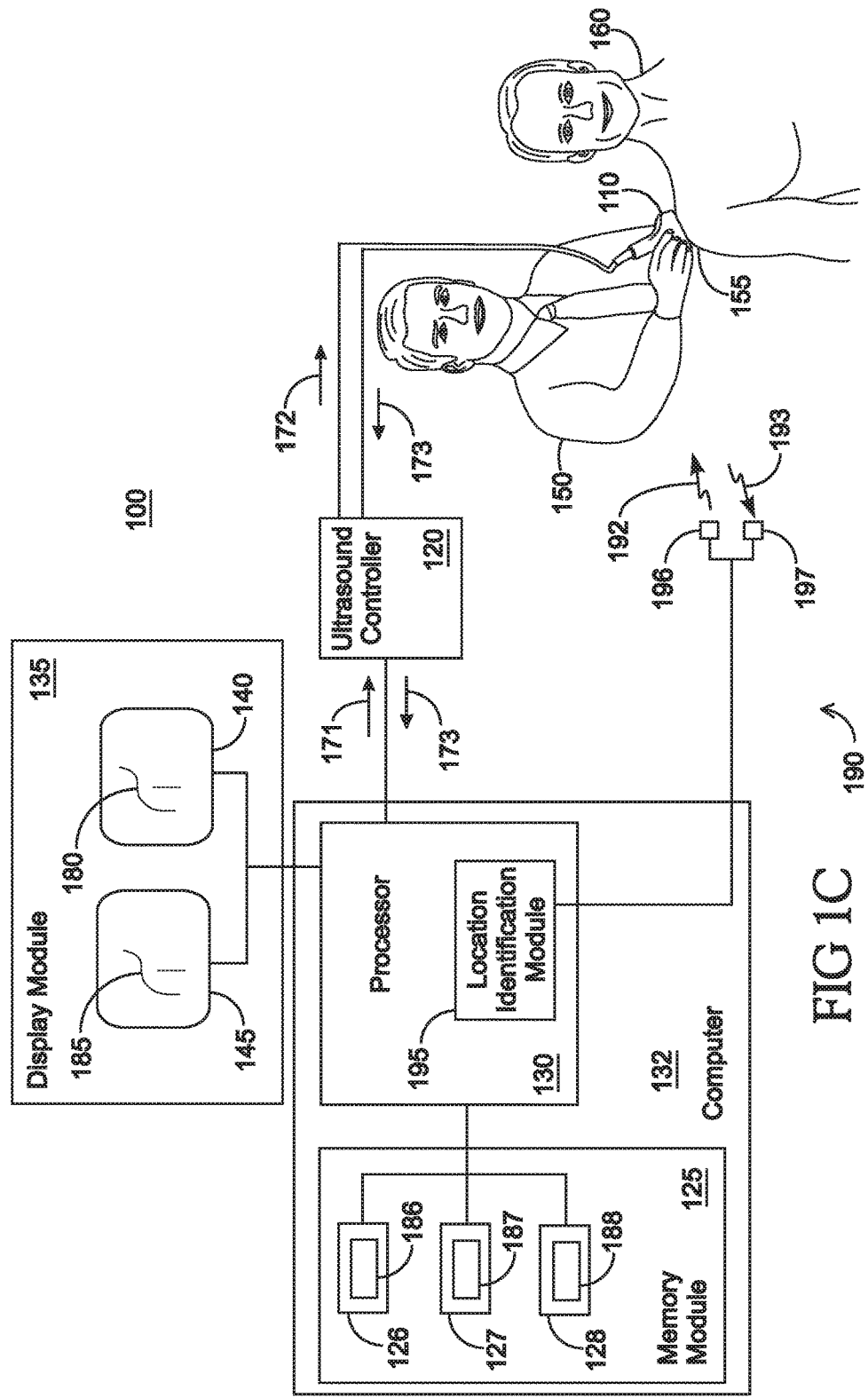
FIG. 1C is a block diagram of still another system for identification of organic specimen features in ultrasound images as described in various representative embodiments.

FIG. 1C is a block diagram of still another system 100 for identification of organic specimen 160 features in ultrasound images 180 as described in various representative embodiments. The system 100 of FIG. 1C differs from that of FIG. 1A in that the ultrasound controller 120 receives the reflected data signal 173 from the ultrasound transducer 110 and then transfers the reflected data signal 173 to the processor 130 either as received or as appropriately modified. The system 100 of FIG. 1C also differs from that of FIG. 1A in that the functions of the location identification module 195 are included in the processor 130 with the emitter device 196 and the receptor device 197 located external to the processor 130. The location detection unit 190 comprises the emitter device 196, the receptor device 197, and the location identification module 195. Again, the activation signal 172 and the reflected data signal 173 will be more completely described with the description of FIG. 2, and various other components of FIG. 1C will be more completely described with the description of subsequent figures.

In alternative embodiments, the location detection unit 190 of FIG. 1A could replace the location detection unit 190 of FIG. 1C in the configuration of FIG. 1C, the location detection unit 190 of FIG. 1C could replace the location detection unit 190 of FIG. 1A in the configuration of FIG. 1A, and the location detection unit 190 of FIG. 1C could replace the location detection unit 190 of FIG. 1B in the configuration of FIG. 1B.

Figure 1D:
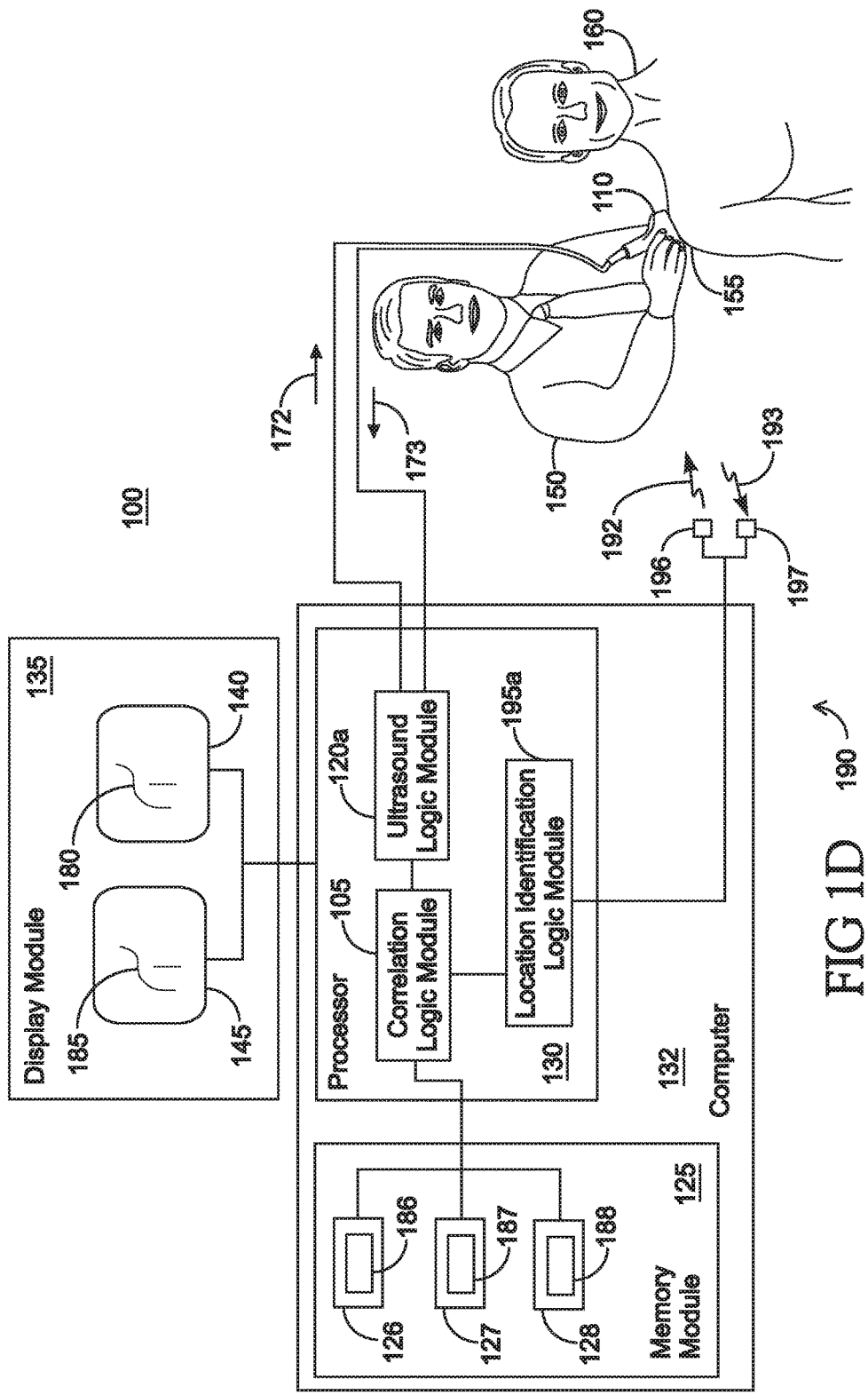
FIG. 1D is a block diagram of yet another system for identification of organic specimen features in ultrasound images as described in various representative embodiments.

FIG. 1D is a block diagram of yet another system for identification of organic specimen 160 features in ultrasound images 180 as described in various representative embodiments. The system 100 of FIG. 1D differs from that of FIG.

1A in that the processor 130 comprises an ultrasound logic module 120a, a location identification logic module 195a, and a correlation logic module 105.

The ultrasound logic module 120a can be configured to perform the functions associated with the ultrasound controller 120 of FIGS. 1A, 1B, and/or 1C and is operatively coupled to the ultrasound transducer 110 and to the correlation logic module 105. upon instructions from the processor 130, the ultrasound logic module 120a initiates transmission of the activation signal 172 to the ultrasound transducer 110 and receives the subsequent reflected data signal 173. The ultrasound logic module 120a then transfers ultrasound data 187 from the reflected data signal 173 to the correlation logic module 105.

Figure 1E:
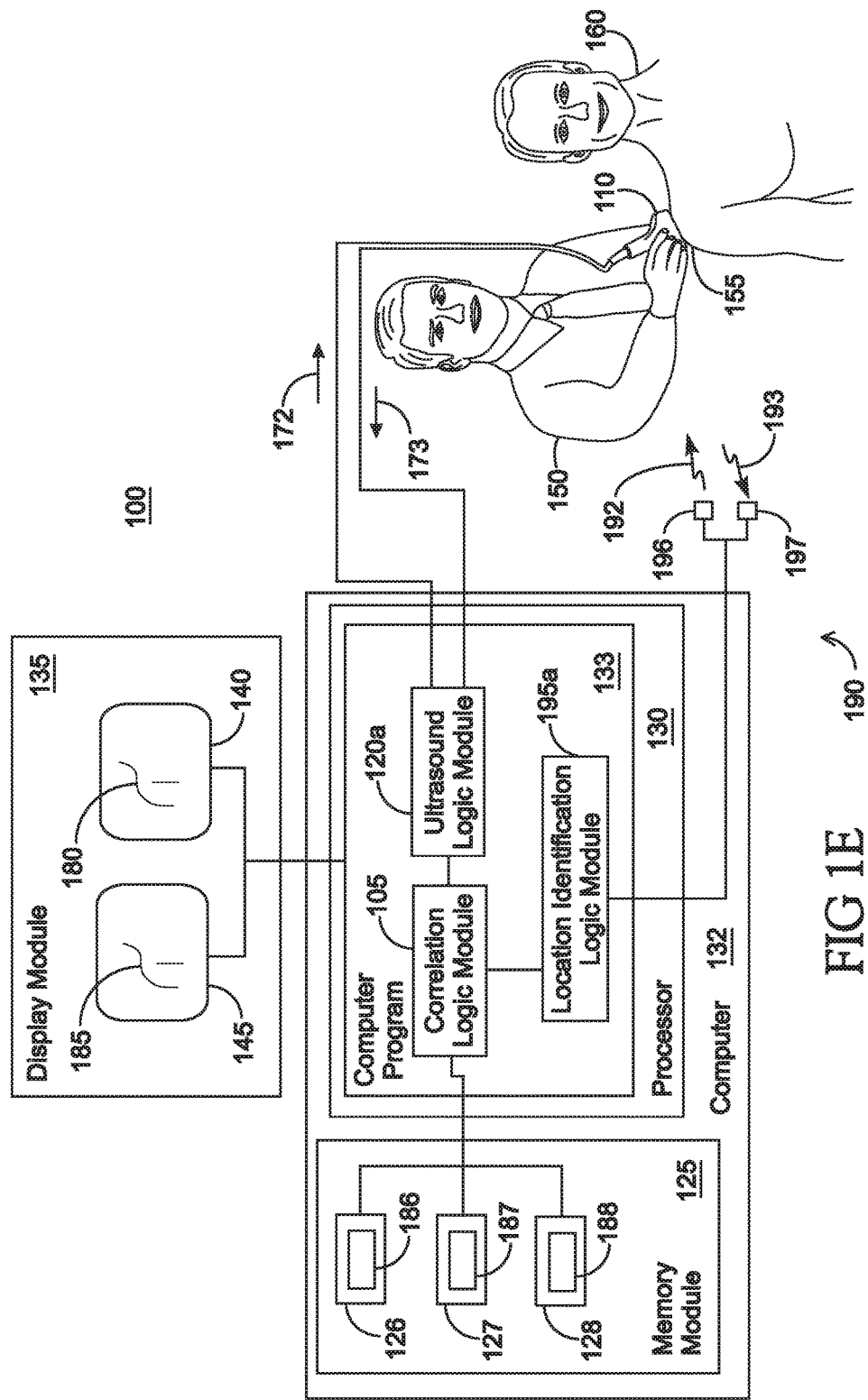
FIG. 1E is a block diagram of yet still another system for identification of organic specimen features in ultrasound images as described in various representative embodiments.

FIG. 1E is a block diagram of yet still another system for identification of organic specimen features in ultrasound images as described in various representative embodiments. The system 100 of FIG. 1E differs from that of FIG. 1D in that the processor 130 comprises a computer program 133 which is also referred to herein as a computer program product 133.

The computer program product 133 comprises instructions for carrying out a method 900 when executed by the processor 130 on the computer 132. The computer program product 133 is stored on a computer readable storage medium which could be the memory module 125 and/or the memory of the processor 130. The computer readable storage medium could be the hard drive of a computer, a floppy disk, a CD, a DVD, a USB chip, a RAM memory, or other acceptable storage medium. In a representative embodiment, the computer program product 133 comprises an ultrasound logic module 120a, a location identification logic module 195a, and a correlation logic module 105. These logic modules comprise instructions for performing a method 900, wherein the method 900 comprises: specifying a reference model image region 520a in model extracted data 188 obtained from anatomic model data 186 of at least part 155 of an organic specimen 160; instructing an ultrasound transducer 110 to transmit ultrasound incident waves 201 into the organic specimen 160 and receiving thereby ultrasound data 187 from ultrasound reflected waves 202 from specimen features 210 in the organic specimen 160, wherein positional awareness 194 of each ultrasound reflected wave 202 relative to the organic specimen 160 is maintained; identifying a reference propagation region 220a corresponding to the reference model image region 520a from paired recognized specimen features 210 in the ultrasound data 187 and in the model extracted data 188; instructing the ultrasound transducer 110 to transmit at least one subsequent ultrasound incident wave 201 into the organic specimen 160 and receiving thereby subsequent ultrasound data 187 from ultrasound reflected waves 202 from one or more specimen features 210, wherein positional awareness is maintained between the reference propagation region 220a and the propagation region 220 of the subsequent ultrasound data 187; and for the subsequent ultrasound data 187, creating an ultrasound image 180, creating a model image 185 for a model image region 520 from the anatomic model data 186 corresponding to the propagation region 220 of the subsequent ultrasound data 187, and instructing a display module 135 to display the ultrasound image 180 and the model image 185.

The location identification logic module 195a is configured to instruct the emitter device 196 to transmit location interrogation signals 192 to transducer targets 230 (see FIG. 2 and discussion therewith) on the ultrasound transducer 110 and to specimen targets 240 (see FIG. 2 and discussion therewith) on an organic specimen 160 which could be a patient 160 and to receive location information from subsequent location information signals 193 received by the receptor device 197. The location identification logic module 195a is further configured to extract location information for the transducer targets 230 and/or the specimen targets 240 from the information in the location information signals 193 and/or from the location interrogation signals 192. This location information is then transferred to the correlation logic module 105. In FIG. 1D, the location detection unit 190 comprises the emitter device 196, the receptor device 197, and the location identification logic module 195a.

The correlation logic module 105 is configured to receive ultrasound data 187 from the ultrasound logic module 120a and location information from the location identification logic module 195a, to obtain model extracted data 188 from the anatomic model data 186 in the memory module 125, to identify a reference model image plane 520a in the model extracted data 188, to identify a corresponding reference propagation plane 220a from recognized specimen features 210 in the ultrasound data 187 and associated location information from the location identification logic module 195a, to receive ultrasound data 187 from subsequent ultrasound reflected waves 202 from one or more specimen features 210 wherein positional awareness is maintained between the reference propagation plane 220a and the propagation plane 220 of the subsequent ultrasound data 187, and for the subsequent ultrasound data 187 to create an ultrasound image 180, to create a model image 185 for a model image plane 520 from the anatomic model data 186 corresponding to the propagation plane 220 of the subsequent ultrasound data 187, and to transfer the ultrasound image 180 and the model image 185 to the display module 135. As appropriate, the correlation logic module 105 can be further configured to store the ultrasound data 187, the model extracted data 188, the ultrasound images 180, and/or the model images 185.

In alternative representative embodiments, the ultrasound logic module 120a, the location identification logic module 195a, and/or the correlation logic module 105 can be implemented in hardware, as a software program, or in firmware either external to or internal to the processor 130. The software program and/or the firmware could be configured to provide instructions to the computer 132 to perform various method steps and/or functions disclosed herein. In other alternative embodiments, the ultrasound logic module 120a, the location identification logic module 195a, and/or the correlation logic module 105 can be replaced respectively by the ultrasound controller 120, the location identification module 195, and or the functions of the processor 130 as in the configurations of FIGS. 1A, 1B, and/or 1C.

FIG. 1F is a block diagram of a system 100 for the identification of corresponding features in ultrasound data 187 obtained from an organic specimen 160 and in anatomic model data 186 for that organic specimen 160 as described in various representative embodiments. The system 100 of FIG. 1F comprises an ultrasound transducer 110, an ultrasound machine 115, a location detection apparatus 191, a combination computer 132-I, an optional client display module 135-C and an optional server display module 135-S. The combination computer 132-I comprises a client computer 132-C, also referred to herein as a second computer 132-C, and a server computer 132-S, also referred to herein as a first computer 132-S.

The client computer 132-C comprises a client memory module 125-C, also referred to herein as a client computer memory 125-C, as a second memory module 125-C, and as a second memory 125-C, and a client processor 130-C, also referred to herein as a second processor 130-C. The client memory module 125-C may store any appropriate data and/or computer programs associated with the disclosed system. The client processor 130-C comprises an ultrasound logic module 120a and a location identification logic module 195a. The client display module 135-C comprises a client ultrasound display 140-C also referred to herein as a first client display 140-C and a client model display 145-C also referred to herein as a second client display 145-C.

The server computer 132-S comprises a server memory module 125-S, also referred to herein as a server computer memory 125-S, as a first memory module 125-S, and as a first memory 125-S, and a server processor 130-S, also referred to herein as a first processor 130-S. The server processor 130-S comprises a correlation logic module 105. The server memory module 125-S comprises an anatomic model memory 126 which is configured to store anatomic model data 186, an ultrasound memory 127 which is configured to store ultrasound data 187 and optionally an extracted model memory 128 configured to store model extracted data 188. The server display module 135-S comprises a server ultrasound display 140-S also referred to herein as a first server display 140-S and a server model display 145-S also referred to herein as a second server display 145-S.

The location detection apparatus 191 comprises an emitter device 196 and a receptor device 197. The ultrasound machine 115 comprises an ultrasound module 116 which could be a signal generator 116, an optional switch 117 and an optional ultrasound machine display 118.

As needed various components of FIG. 1F may be coupled via appropriately located and configured input/output devices (I/O devices) 199 which are not explicitly shown in any of the figures.

The ultrasound transducer 110 is coupled to the ultrasound module 116 in the ultrasound machine 115. The switch 117 is optionally coupled to the ultrasound module 116, and the ultrasound machine display 118 is optionally coupled to the ultrasound module 116. The ultrasound module 116 of the ultrasound machine 115 is coupled to the client computer 132-C with subsequent coupling to the client processor 130-C within the client computer 132-C and then to the ultrasound logic module 120a in the client processor 130-C. The location detection apparatus 191 is coupled to the client computer 132-C with subsequent coupling to the client processor 130-C within the client computer 132-C and then to the location identification logic module 195a in the client processor 130-C. The client processor 130-C is optionally coupled to the client display module 135-C.

The client computer 132-C is coupled to the server computer 132-S which may be either remotely located from or locally located with the client computer 132-C. A remotely located server computer 132-S could be hosted on the Internet or other network to store, manage and process data received from the client computer 132-C.

The ultrasound logic module 120a and the location identification logic module 195a are coupled to the correlation logic module 105 in the server processor 130-S of the server computer 132-S. The correlation logic module 105 is configured to access data from and store data in the server memory module 125-S.

Figure 2:
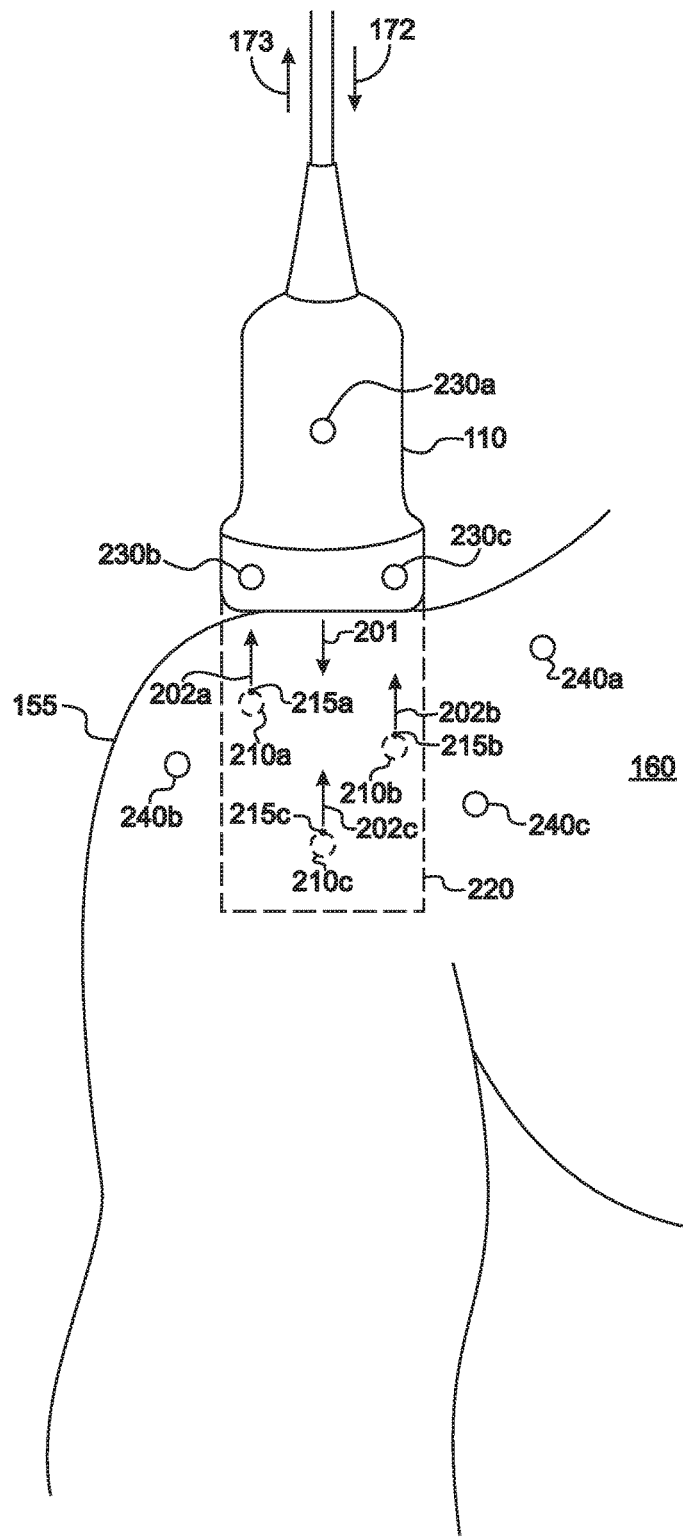
FIG. 2 is a front view of the patient of FIGS. 1A, 1B, 1C, 1D, 1E, 1F, 1G, 1H and 1I with the ultrasound transducer coupled to the shoulder of the patient.

In representative embodiments, in response to an initiation signal 171 from the ultrasound logic module 120a the ultrasound module 116 transmits an activation signal 172 to the ultrasound transducer 110 to transmit one or more ultrasound incident waves 201 into the organic specimen 160 receiving thereby via the ultrasound transducer 110 one or more reflected data signals 173 from one or more associated ultrasound reflected waves 202 reflected from specimen features 210 in the organic specimen 160 (see FIG. 2 and discussion therewith). In an alternative representative embodiment, activation signals 172 to the ultrasound transducer 110 could be initiated by the ultrasound module 116. In another representative embodiment, the ultrasound module 116 could be free running. Further, the ultrasound transducer 110 could be configured to control enablement of transmission of ultrasound incident waves 201 essentially performing a freeze frame common to current commercial ultrasound machines. Reflected data signals 173 are coupled to the ultrasound logic module 120a and can be displayed in appropriate format on the ultrasound machine display 118. The switch 117 could be activated by the operator 150 or by other means to select one or more specific reflected data signals 173 to transfer to the ultrasound logic module 120a thereby limiting the data to be processed. The switch 117 could be, for example, a foot switch 117, a rocker arm switch 117, a toggle switch 117, push-button switch 117, or any other appropriate switch mechanism 117.

The location detection apparatus 191 is configured to instruct the emitter device 196 to transmit location interrogation signals 192 to transducer targets 230 on the ultrasound transducer 110 and to specimen targets 240 on an organic specimen 160 which could be a patient 160. Upon reception of the location interrogation signals 192 by the transducer targets 230 and the specimen targets 240, the transducer targets 230 and the specimen targets 240 separately respond with location information signals 193 which can be received by the receptor device 197 (see FIG. 2 and discussion therewith). Information from the location information signals 193 received by the receptor device 197 is transferred from the receptor device 197 to the location identification logic module 195a. The location identification logic module 195a is further configured to extract location information for the transducer targets 230 and the specimen targets 240 from the information in the location information signals 193 and/or from the location interrogation signals 192. The extracted location information for the transducer targets 230 and the specimen targets 240 is transferred to the correlation logic module 105 in the server processor 130-S of the server computer 132-S as location data 194.

Both the reflected data signals 173 and the location data 194 could be, for example, tagged with a date-time stamp using the clock of the client computer 132-C so that both signals could be appropriately associated with each other, or they could be associated by any other appropriate means. The reflected data signals 173 could be, for example, tagged with a date-time stamp by the ultrasound logic module 120a being outputted from that module as tagged reflected data signals 179, and the location data 194 could be, for example, tagged with a date-time stamp by the location identification logic module 195a. Both the tagged reflected data signals 179 and the location data 194 are transferred to the server computer 132-S.

Coupling between the various components of the system 100 could be via electronic cables, optical fibers, radio frequency transmitters/receivers, infrared transmitter/receivers, or other appropriate means for transmitting or transferring signals.

The location data 194 can be used by the correlation logic module 105 in the server processor 130-S to associate a specific set of ultrasound data 187 with the relative locations and orientations of the ultrasound transducer 110 and the organic specimen 160 for which that set of ultrasound data 187 was obtained. The location data 194 can also be used by the server processor 130-S to obtain a set of model extracted data 188 from the anatomic model data 186 for the region from which the set of ultrasound data 187 is obtained. This set of model extracted data 188 is thereby associated with that set of ultrasound data 187.

The ultrasound memory 127 is configured to store the one or more sets of ultrasound data 187 obtained from the ultrasound transducer 110. The anatomic model memory 126 is configured to store anatomic model data 186 which is a model of and representative of at least part 155 of an organic specimen 160. The extracted model memory 128 is configured to store sets of model extracted data 188. In representative embodiments, a set of model extracted data 188 can be obtained from the anatomic model data 186 for each set of ultrasound data 187 and can be associated with each set of ultrasound data 187. Each associated set of ultrasound data 187 and model extracted data 188 can be used to create associated ultrasound and model images 180,185 wherein the model image 185 is a model of the region from which the ultrasound image 180 is obtained. Again a model image 185 is also referred to herein as model image data 185. The terms ultrasound image 180 and ultrasound image data 180 generally refer to data sets or data streams which are representative of at least a portion of an organic specimen 160. They may or may not be intended for or in a format for visual presentation on a display. The terms model image 185 and model image data 185 generally refer to data sets or data streams which are representative of at least a portion of a model of an organic specimen 160. They may or may not be intended for or in a format for visual presentation on a display. The server processor 130-S is configured to obtain the appropriate set of model extracted data 188 and correlate it with its associated set of ultrasound data 187. In an alternate representative embodiment, the model image 185 can be created from the set of model extracted data 188 without storage of the model extracted data 188. And in another alternate representative embodiment, the set of ultrasound data 187 and the set of model extracted data 188 are stored jointly in a single memory which could be the ultrasound memory 127. The ultrasound image 180 can be transferred to the client computer 132-C and displayed there on the client ultrasound display 140-C, and concurrently the model image 185 associated with the ultrasound image 180 can be transferred to the client computer 132-C and displayed there on the client model display 145-C. The ultrasound image 180 can also be displayed on the server ultrasound display 140-S, and concurrently the model image 185 associated with the ultrasound image 180 can be displayed on the server model display 145-S.

In representative embodiments, an operator 150 holds the ultrasound transducer 110 against, for example, a shoulder 155 of a patient 160. The patient 160 shown in FIG. 1F could more generally be any organic specimen 160 and more particularly could be a person 160, a baby 160, another animal 160, a plant 160 or the like. However, the term organic specimen 160 as used herein more generally means any living or deceased organism or any portion of a living or deceased organism. In particular, the organic specimen could be a human, another animal, a plant, a portion of a human, a portion of another animal, or a portion of a plant. The shoulder 155 shown in FIG. 1F could more generally be a part 155 of any organic specimen 160. The initiation signal 171, the activation signal 172 and reflected data signal 173 will be more completely described with the description of FIG. 2. The anatomic model data 186 stored in the server memory module 125-S could be anatomic model data 186 of at least part 155 of the organic specimen 160. In representative embodiments, the anatomic model data 186 could be obtained, for example, from the Visible Human Project® (VHP) or other appropriate data which can be used, for example, to create two-dimensional model images 185 of a representative human body (male or female) at diverse selected depths and angular orientations. The VHP data and other model data sources could be used to create static two-dimensional, static three-dimensional, time varying two-dimensional, and/or time varying three-dimensional model images 185. Various components of FIG. 1F will be more completely described with the description of subsequent figures.

While the representative embodiments disclosed herein are discussed in terms of static two-dimensional model and ultrasound images 185,180, the representative embodiments can also be implemented using time varying two-dimensional model and ultrasound images 185,180, static three-dimensional model and ultrasound images 185,180, and time varying three-dimensional model and ultrasound images 185,180. As appropriate, these images can be displayed, for example, on a two-dimensional display system as static or time varying two-dimensional images and on a three-dimensional display system as static or time varying three-dimensional images.

Figure 1G:
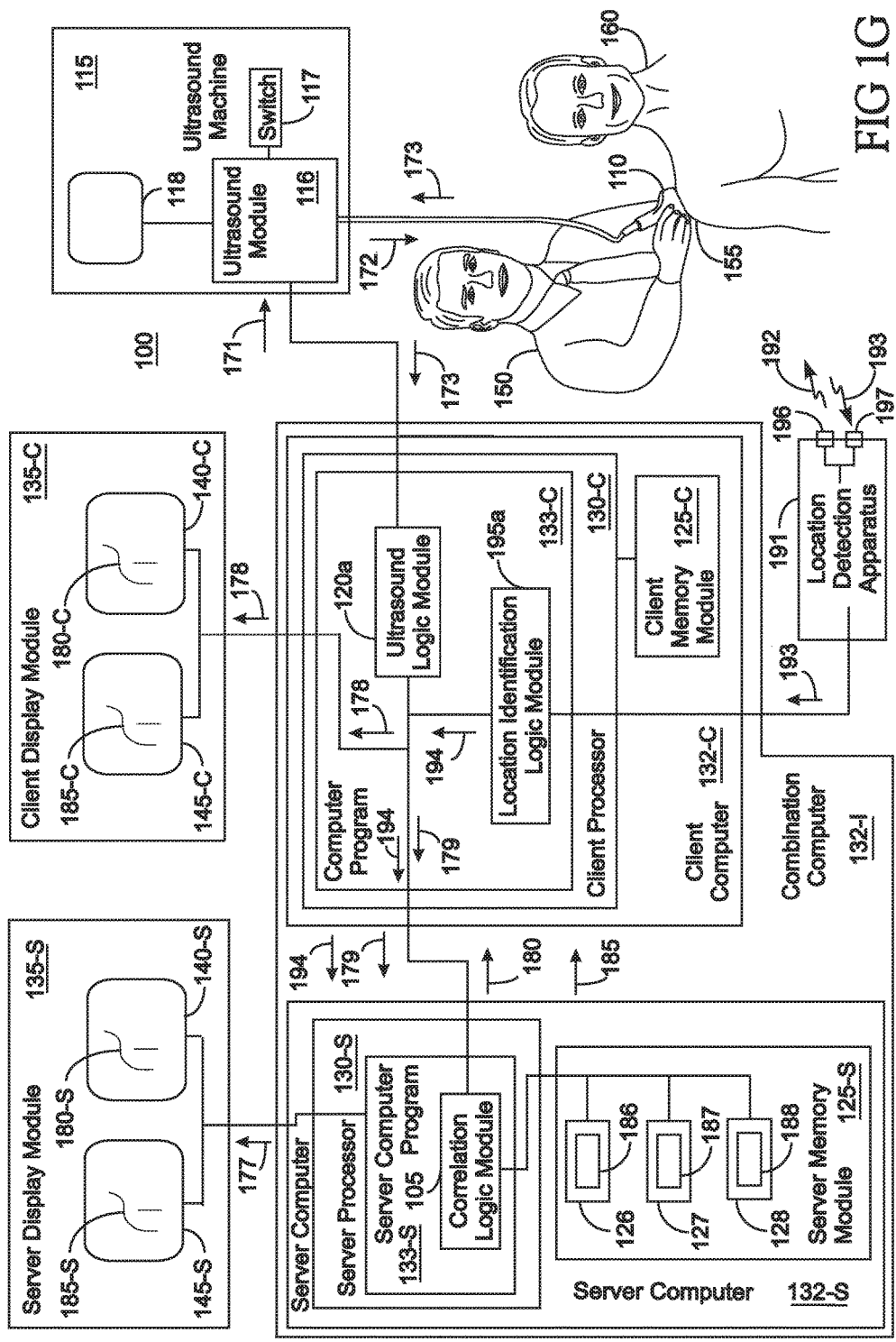
FIG. 1G is a block diagram of another system for the identification of corresponding features in ultrasound data obtained from an organic specimen and in model data for that organic specimen as described in various representative embodiments.

FIG. 1G is a block diagram of another system 100 for the identification of corresponding features in ultrasound data 187 obtained from an organic specimen 160 and in anatomic model data 186 for that organic specimen 160 as described in various representative embodiments. The system 100 of FIG. 1G is similar to but differs from that of FIG. 1F in that the client processor 130-C comprises a client computer program 133-C, also referred to herein as a client computer program product 133-C, as a second computer program 133-C, and as a second computer program product 133-C, and a server computer program 133-S, also referred to herein as a server computer program product 133-S, as a first computer program 133-S, and as a first computer program product 133-S, The client computer program product 133-C comprises instructions for carrying out parts of methods 1000,1100, 1200 when executed by the client processor 130-C on the client computer 132-C (see FIGS. 10, 11, and 12 and discussion therewith). The client computer program product 133-C is stored on a computer readable storage medium which could be the client memory module 125-C and/or the memory of the client processor 130-C.

Figure 10:
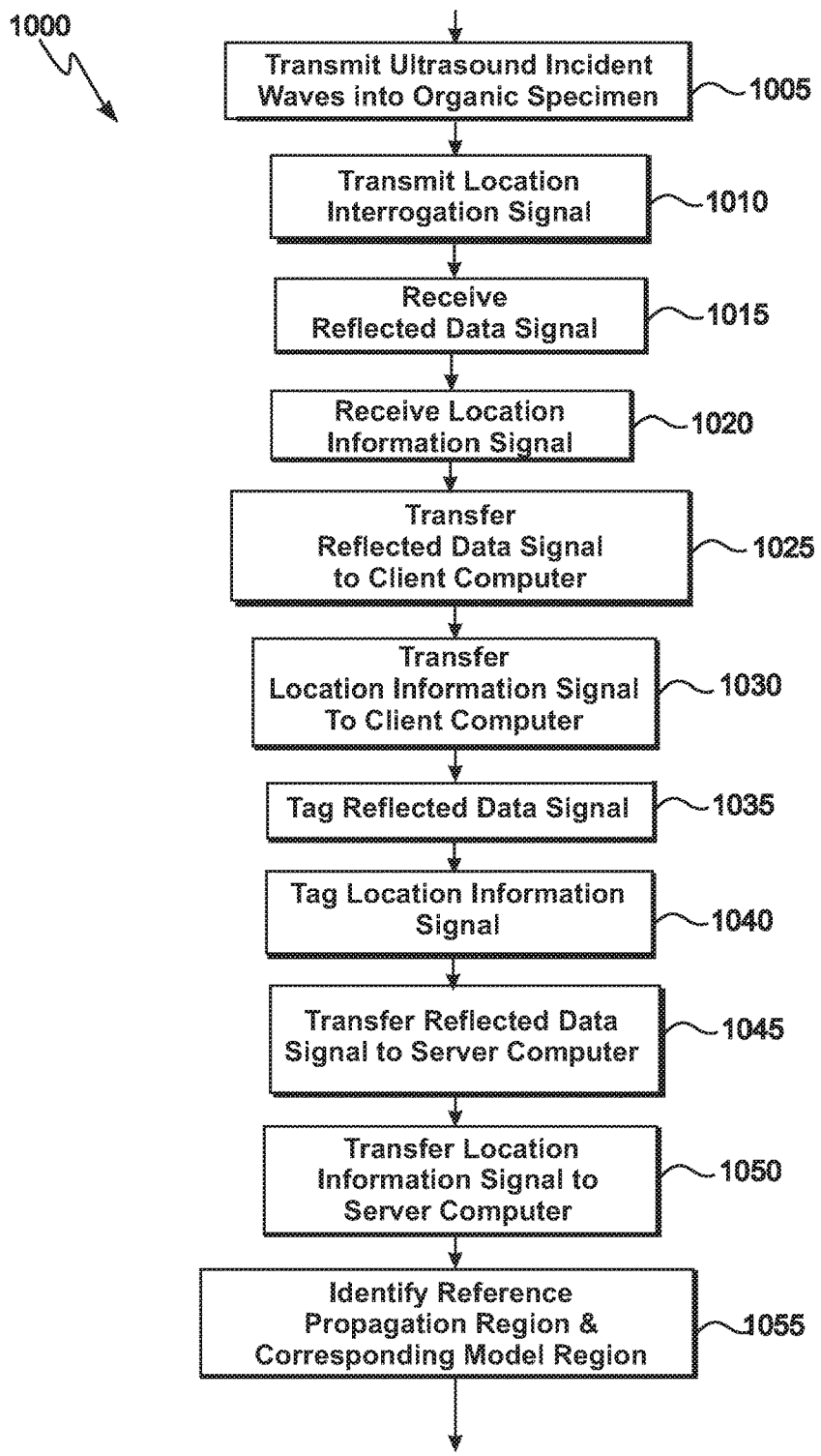
FIG. 10 is a flow chart of a segment of a method for the identification of organic specimen features in ultrasound data using a client computer and a server computer as described in various representative embodiments.
Figure 11:
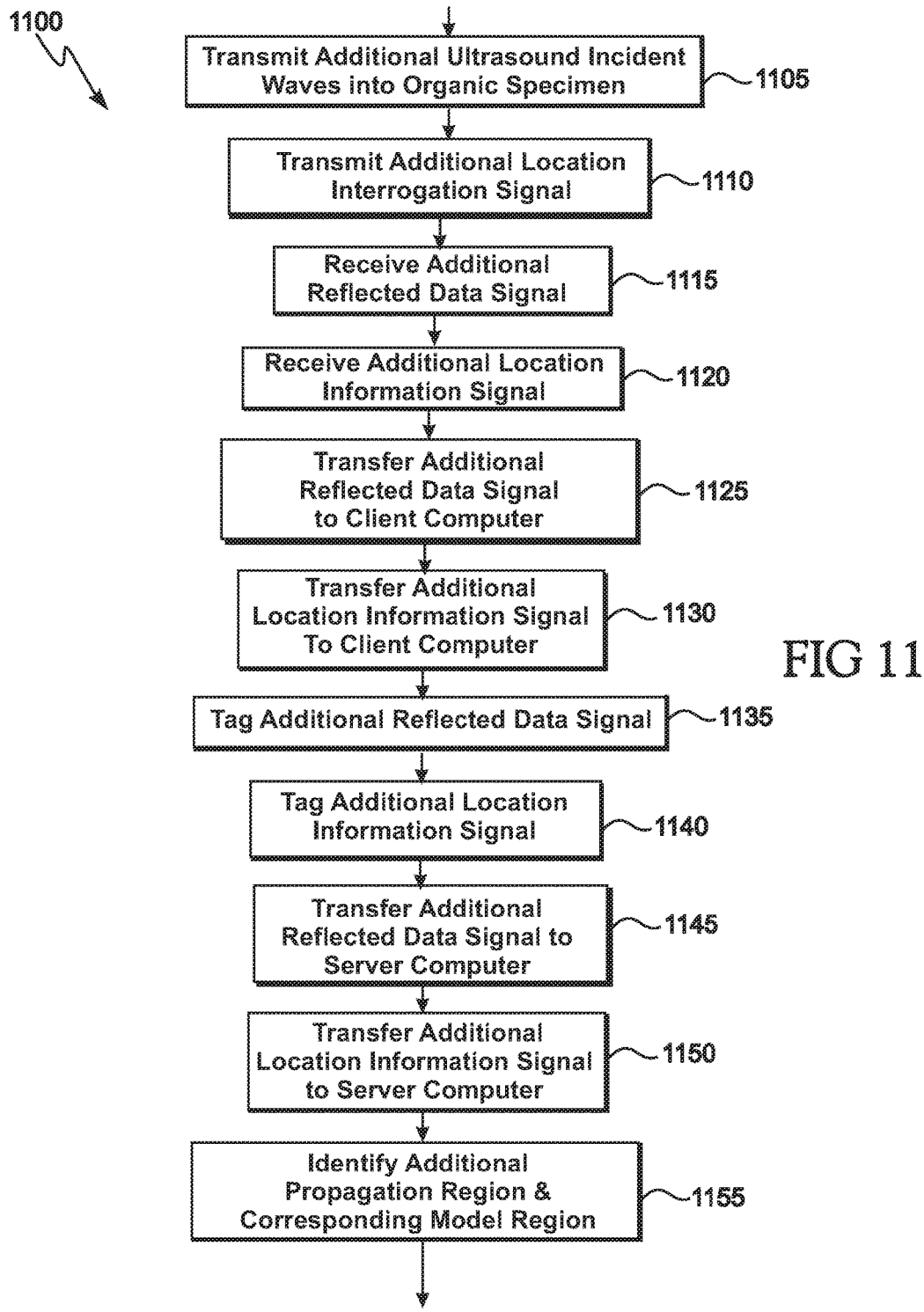
FIG. 11 is a flow chart of another segment of a method for the identification of organic specimen features in ultrasound data using a client computer and a server computer as described in various representative embodiments.
Figure 12:
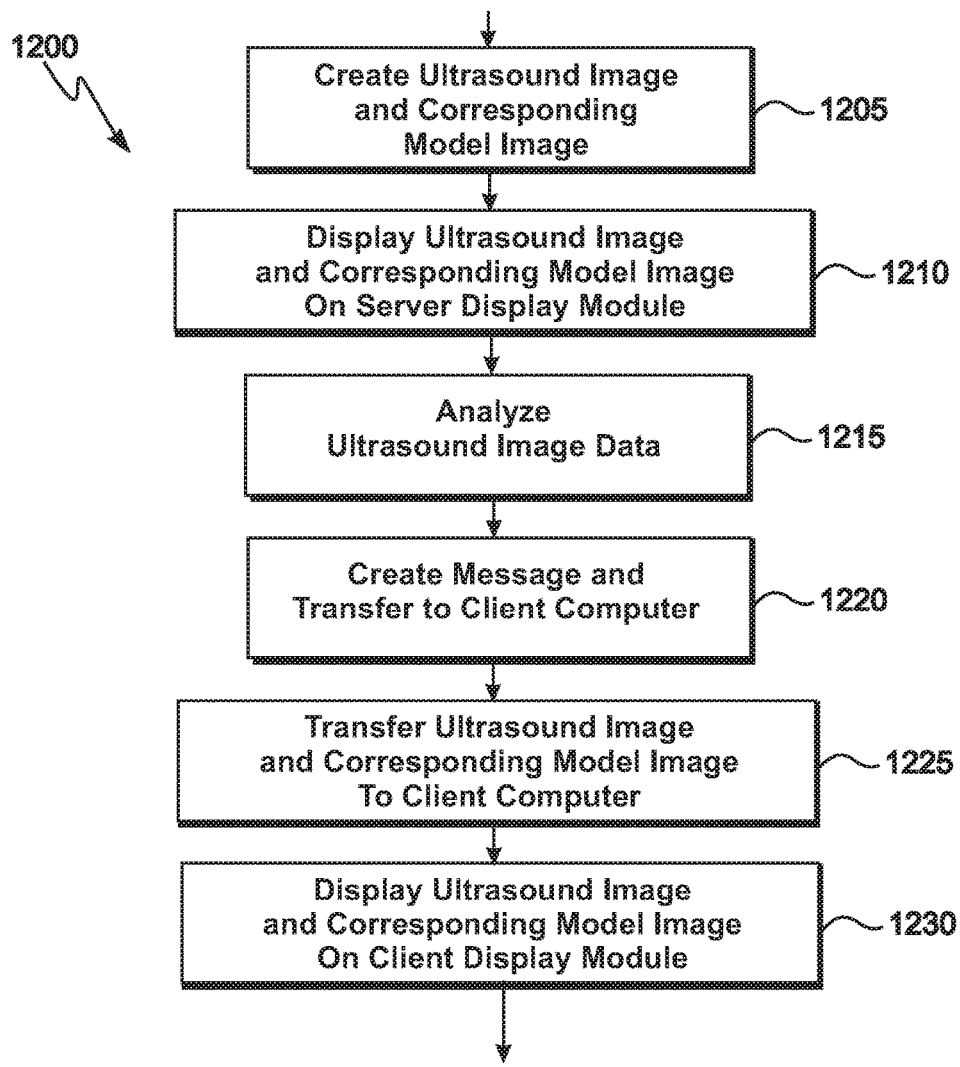
FIG. 12 is a flow chart of still another segment of a method for the identification of organic specimen features in ultrasound data using a client computer and a server computer as described in various representative embodiments.

The server computer program product 133-S comprises instructions for carrying out parts of methods 1000,1100, 1200 when executed by the server processor 130-S on the server computer 132-S (see FIGS. 10, 11, and 12 and discussion therewith). The server computer program product 133-S is stored on a computer readable storage medium which could be the server memory module 125-S and/or the memory of the server processor 130-S. The computer readable storage medium for the client computer program product 133-C and the server computer program product 133-S could separately and independently be the hard drive of a computer, a floppy disk, a CD, a DVD, a USB chip, a RAM memory, or other acceptable storage medium.

In a representative embodiment, the client computer program product 133-C comprises an ultrasound logic module 120a and a location identification logic module 195a, and the server computer program product 133-S comprises a correlation logic module 105. As previously stated the logic modules of the client computer program product 133-C and the server computer program product 133-S comprise instructions for performing the methods 1000, 1100 and 1200 and functions similar to that of FIG. 1F.

Figure 1H:
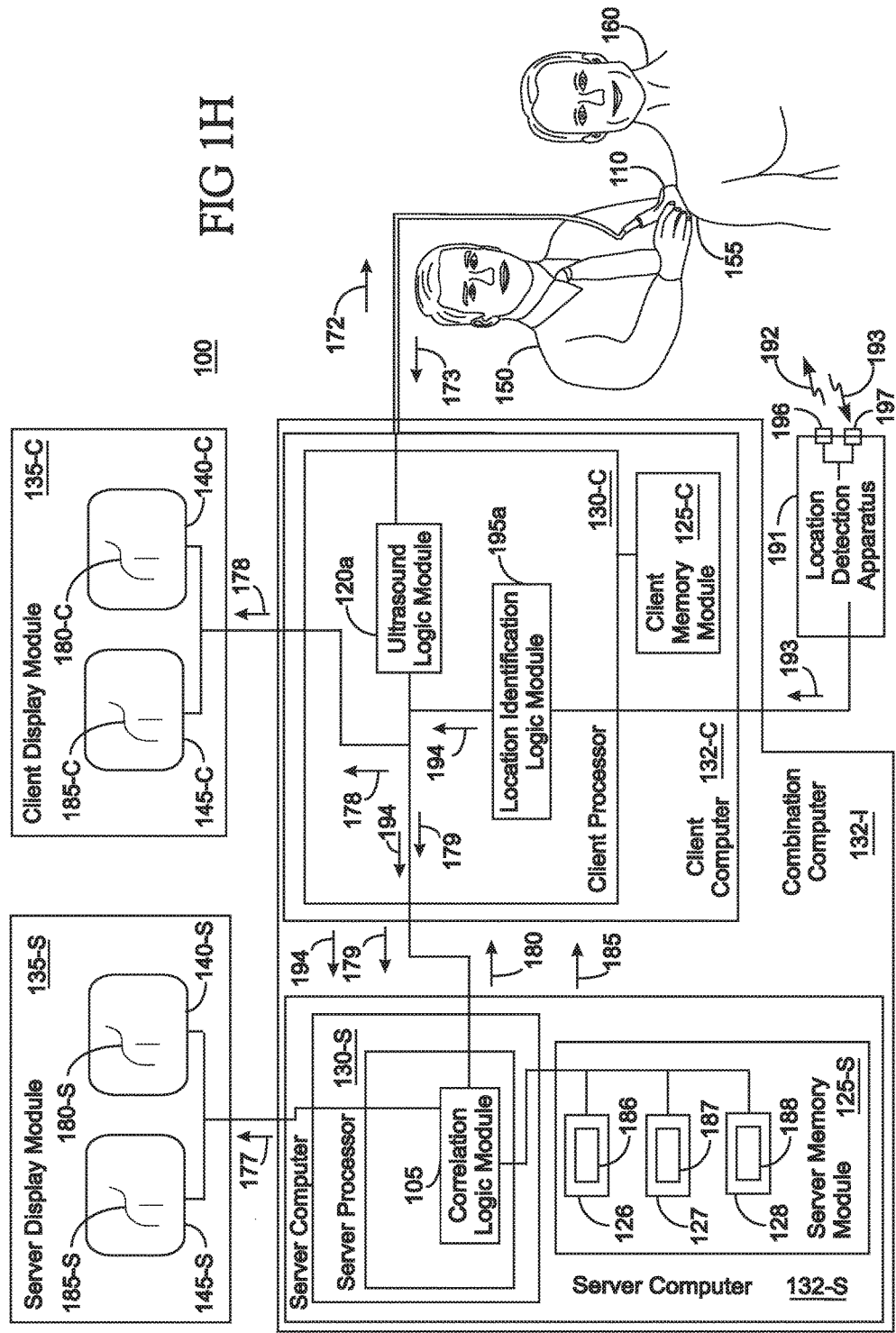
FIG. 1H is a block diagram of still another system for the identification of corresponding features in ultrasound data obtained from an organic specimen and in model data for that organic specimen as described in various representative embodiments.

FIG. 1H is a block diagram of still another system 100 for the identification of corresponding features in ultrasound data 187 obtained from an organic specimen 160 and in anatomic model data 186 for that organic specimen 160 as described in various representative embodiments. The system 100 of FIG. 1H comprises an ultrasound transducer 110, a location detection apparatus 191, a combination computer 132-I, an optional client display module 135-C and an optional server display module 135-S. The combination computer 132-I comprises a client computer 132-C, also referred to herein as a second computer 132-C, and a server computer 132-S also referred to herein as a first computer 132-S.

The client computer 132-C comprises a client memory module 125-C, also referred to herein as a client computer memory 125-C, as a second memory module 125-C, and as a second memory 125-C, and a client processor 130-C, also referred to herein as a second processor 130-C. The client memory module 125-C may store any appropriate data and/or computer programs associated with the disclosed system. The client processor 130-C comprises an ultrasound logic module 120a and a location identification logic module 195a. The client display module 135-C comprises a client ultrasound display 140-C also referred to herein as a first client display 140-C and a client model display 145-C also referred to herein as a second client display 145-C.

The server computer 132-S comprises a server memory module 125-S, also referred to herein as a server computer memory 125-S, as a first memory module 125-S, and as a first memory 125-S, and a server processor 130-S, also referred to herein as a first processor 130-S. The server processor 130-S comprises a correlation logic module 105. The server memory module 125-S comprises an anatomic model memory 126 which is configured to store anatomic model data 186, an ultrasound memory 127 which is configured to store ultrasound data 187 and optionally an extracted model memory 128 configured to store model extracted data 188. The server display module 135-S comprises a server ultrasound display 140-S also referred to herein as a first server display 140-S and a server model display 145-S also referred to herein as a second server display 145-S.

The location detection apparatus 191 comprises an emitter device 196 and a receptor device 197.

As needed various components of FIG. 1H may be coupled via appropriately located and configured input/output devices (I/O devices) 199 which are not explicitly shown in any of the figures.

The ultrasound transducer 110 is coupled to the client computer 132-C with subsequent coupling to the client processor 130-C within the client computer 132-C and then to the ultrasound logic module 120a in the client processor 130-C. The location detection apparatus 191 is coupled to the client computer 132-C with subsequent coupling to the client processor 130-C within the client computer 132-C and then to the location identification logic module 195a in the client processor 130-C. The client processor 130-C is optionally coupled to the client display module 135-C.

The client computer 132-C is coupled to the server computer 132-S which may be either remotely located from or locally located with the client computer 132-C. A remotely located server computer 132-S could be hosted on the Internet or other network to store, manage and process data received from the client computer 132-C.

The ultrasound logic module 120a and the location identification logic module 195a are coupled to the correlation logic module 105 in the server processor 130-S of the server computer 132-S. The correlation logic module 105 is configured to access data from and store data in the server memory module 125-S.

In representative embodiments, the ultrasound logic module 120a transmits an activation signal 172 to the ultrasound transducer 110 to transmit one or more ultrasound incident waves 201 into the organic specimen 160 receiving thereby via the ultrasound transducer 110 one or more reflected data signals 173 from one or more associated ultrasound reflected waves 202 reflected from specimen features 210 in the organic specimen 160 (see FIG. 2 and discussion therewith). Further, the ultrasound transducer 110 could be configured to control enablement of transmission of ultrasound incident waves 201. Reflected data signals 173 are coupled to the ultrasound logic module 120a and can be displayed in appropriate format on the client ultrasound display 140-C. A switch 117 which is not shown in FIG. 1H could be located on the client computer 132-C, on the ultrasound transducer 110 or other appropriate location and could be activated by the operator 150 or by other means to select one or more specific reflected data signals 173 to transfer to the ultrasound logic module 120a thereby limiting the data to be processed. The switch 117 could be, for example, a foot switch 117, a rocker arm switch 117, a toggle switch 117, push-button switch 117, or any other appropriate switch 117.

The location detection apparatus 191 is configured to instruct the emitter device 196 to transmit location interrogation signals 192 to transducer targets 230 on the ultrasound transducer 110 and to specimen targets 240 on an organic specimen 160 which could be a patient 160. Upon reception of the location interrogation signals 192 by the transducer targets 230 and the specimen targets 240, the transducer targets 230 and the specimen targets 240 separately respond with location information signals 193 which can be received by the receptor device 197 (see FIG. 2 and discussion therewith). Information from the location information signals 193 received by the receptor device 197 is transferred from the receptor device 197 to the location identification logic module 195a. The location identification logic module 195a is further configured to extract location information for the transducer targets 230 and the specimen targets 240 from the information in the location information signals 193 and/or from the location interrogation signals 192. The extracted location information for the transducer targets 230 and the specimen targets 240 is transferred to the correlation logic module 105 in the server processor 130-S of the server computer 132-S as location data 194

Both the reflected data signals 173 and the location data 194 could be, for example, tagged with a date-time stamp using the clock of the client computer 132-C so that both signals could be appropriately associated with each other, or they could be associated by any other appropriate means. The reflected data signals 173 could be, for example, tagged with a date-time stamp by the ultrasound logic module 120a being outputted from that module as tagged reflected data signals 179, and the location data 194 could be, for example, tagged with a date-time stamp by the location identification logic module 195a. Both the tagged reflected data signals 179 and the location data 194 are transferred to the server computer 132-S.

Coupling between the various components of the system 100 could be via electronic cables, optical fibers, radio frequency transmitters/receivers, infrared transmitter/receivers, or other appropriate means for transmitting or transferring signals.

The location data 194 can be used by the correlation logic module 105 in the server processor 130-S to associate a specific set of ultrasound data 187 with the relative locations and orientations of the ultrasound transducer 110 and the organic specimen 160 for which that set of ultrasound data 187 was obtained. The location data 194 can also be used by the server processor 130-S to obtain a set of model extracted data 188 from the anatomic model data 186 for the region from which the set of ultrasound data 187 is obtained. This set of model extracted data 188 is thereby associated with that set of ultrasound data 187.

The ultrasound memory 127 is configured to store the one or more sets of ultrasound data 187 obtained from the ultrasound transducer 110. The anatomic model memory 126 is configured to store anatomic model data 186 which is a model of and representative of at least part 155 of an organic specimen 160. The extracted model memory 128 is configured to store sets of model extracted data 188. In representative embodiments, a set of model extracted data 188 can be obtained from the anatomic model data 186 for each set of ultrasound data 187 and can be associated with each set of ultrasound data 187. Each associated set of ultrasound data 187 and model extracted data 188 can be used to create associated ultrasound and model images 180,185 wherein the model image 185 is a model of the region from which the ultrasound image 180 is obtained. And again model image 185 is also referred to herein as model image data 185. The terms ultrasound image 180 and ultrasound image data 180 generally refer to data sets or data streams which are representative of at least a portion of an organic specimen 160. They may or may not be intended for or in a format for visual presentation on a display. The terms model image 185 and model image data 185 generally refer to data sets or data streams which are representative of at least a portion of a model of an organic specimen 160. They may or may not be intended for or in a format for visual presentation on a display. The server processor 130-S is configured to obtain the appropriate set of model extracted data 188 and correlate it with its associated set of ultrasound data 187. In an alternate representative embodiment, the model image 185 can be created from the set of model extracted data 188 without storage of the model extracted data 188. And in another alternate representative embodiment, the set of ultrasound data 187 and the set of model extracted data 188 are stored jointly in a single memory which could be the ultrasound memory 127. The ultrasound image 180 can be transferred to the client computer 132-C and displayed there on the client ultrasound display 140-C, and concurrently the model image 185 associated with the ultrasound image 180 can be transferred to the client computer 132-C and displayed there on the client model display 145-C. The ultrasound image 180 can also be displayed on the server ultrasound display 140-S, and concurrently the model image 185 associated with the ultrasound image 180 can be displayed on the server model display 145-S.

In representative embodiments, an operator 150 holds the ultrasound transducer 110 against, for example, a shoulder 155 of a patient 160. The patient 160 shown in FIG. 1H could more generally be any organic specimen 160 and more particularly could be a person 160, a baby 160, another animal 160, a plant 160 or the like. However, the term organic specimen 160 as used herein more generally means any living or deceased organism or any portion of a living or deceased organism. In particular, the organic specimen could be a human, another animal, a plant, a portion of a human, a portion of another animal, or a portion of a plant. The shoulder 155 shown in FIG. 1H could more generally be a part 155 of any organic specimen 160. The activation signal 172 and the reflected data signal 173 will be more completely described with the description of FIG. 2. The anatomic model data 186 stored in the server memory module 125-S could be anatomic model data 186 of at least part 155 of the organic specimen 160. In representative embodiments, the anatomic model data 186 could be obtained, for example, from the Visible Human Project® (VHP) or other appropriate data which can be used, for example, to create two-dimensional model images 185 of a representative human body (male or female) at diverse selected depths and angular orientations. The VHP data and other model data sources could be used to create static two-dimensional, static three-dimensional, time varying two-dimensional, and/or time varying three-dimensional model images 185. Various components of FIG. 1H will be more completely described with the description of subsequent figures.

While the representative embodiments disclosed herein are discussed in terms of static two-dimensional model and ultrasound images 185,180, the representative embodiments can also be implemented using time varying two-dimensional model and ultrasound images 185,180, static three-dimensional model and ultrasound images 185,180, and time varying three-dimensional model and ultrasound images 185,180. As appropriate, these images can be displayed, for example, on a two-dimensional display system as static or time varying two-dimensional images and on a three-dimensional display system as static or time varying three-dimensional images.

FIG. 1I is a block diagram of yet another system 100 for the identification of corresponding features in ultrasound data 187 obtained from an organic specimen 160 and in anatomic model data 186 for that organic specimen 160 as described in various representative embodiments. The system 100 of FIG. 1I is similar to but differs from that of FIG. 1H in that the client processor 130-C comprises a client computer program 133-C, also referred to herein as a client computer program product 133-C, as a second computer program 133-C, and as a second computer program product 133-C, and a server computer program 133-S, also referred to herein as a server computer program product 133-S, a first computer program 133-S, and as a first computer program product 133-S.

The client computer program product 133-C comprises instructions for carrying out parts of methods 1000,1100, 1200 when executed by the client processor 130-C on the client computer 132-C (see FIGS. 10, 11, and 12 and discussion therewith). The client computer program product 133-C is stored on a computer readable storage medium which could be the client memory module 125-C and/or the memory of the client processor 130-C.

The server computer program product 133-S comprises instructions for carrying out parts of methods 1000,1100, 1200 when executed by the server processor 130-S on the server computer 132-S (see FIGS. 10, 11, and 12 and discussion therewith). The server computer program product 133-S is stored on a computer readable storage medium which could be the server memory module 125-S and/or the memory of the server processor 130-S. The computer readable storage medium for the client computer program product 133-C and the server computer program product 133-S could separately and independently be the hard drive of a computer, a floppy disk, a CD, a DVD, a USB chip, a RAM memory, or other acceptable storage medium.

In a representative embodiment, the client computer program product 133-C comprises an ultrasound logic module 120a and a location identification logic module 195a, and the server computer program product 133-S comprises a correlation logic module 105. As previously stated the logic modules of the client computer program product 133-C and the server computer program product 133-S comprise instructions for performing the methods 1000, 1100 and 1200 and functions similar to that of FIG. 1H.

FIG. 2 is a front view of the patient 160 of FIGS. 1A, 1B, 1C, 1D, 1E, 1F, 1G, 1H and 1I with the ultrasound transducer 110 coupled to the shoulder 155 of the patient 160. In the embodiment of FIG. 2, the activation signal 172 is transferred to the ultrasound transducer 110 which converts it to an ultrasound incident wave 201 and then transmits the ultrasound incident wave 201 into the shoulder 155 of the patient 160 in a propagation plane 220. The propagation plane 220 is considered in an ideal sense to extend to infinity in two dimensions. However, only that part of the propagation plane 220 into which the ultrasound incident wave 201 is transmitted is shown in FIG. 2. The ultrasound incident wave 201 is reflected by various specimen features 210, as well as patient unique features 450 (see FIG. 4 and discussion therewith) which are also referred to herein as organic specimen unique features 450, in the patient's shoulder 155 as ultrasound reflected waves 202. A patient unique feature 450 could be a pathologic feature 450 such as a muscle tear, a tendon tear such as a rotator cuff tear, a nerve problem, a blood clot in the vascular system, or the like, or it could be a foreign object 450 such as a metallic pin affixed to a broken bone in the patient 160 or the like. The ultrasound reflected waves 202 are detected by the ultrasound transducer 110 and converted into a reflected data signal 173 which is in turn transferred back to the processor 130. The plane of the ultrasound image 180 created from the reflected data signal 173 is from features in the propagation plane 220 and, thus, the propagation plane 220 is also the plane of the ultrasound image 180 and is also referred to as the ultrasound image plane 220.

The three specimen features 210a,210b,210c (first specimen feature 210a, second specimen feature 210b, and third specimen feature 210c) separately reflect that part of the ultrasound incident wave 201 incident on them as associated ultrasound reflected waves 202a,202b,202c (first ultrasound reflected wave 202a, second ultrasound reflected wave 202b, and third ultrasound reflected wave 202c). In the representative embodiment of FIG. 2, these three specimen features 210a,210b,210c have separately identifiable specimen reference points 215 (first specimen reference point 215a, second specimen reference point 215b, and third specimen reference point 215c) that together specify a reference propagation plane 220a which is used for specifying the location of and identification of additional, detected specimen features 210. The three specimen features 210a,210b, 210c and their associated specimen reference points 215a, 215b,215c in the representative embodiment of FIG. 2 are shown for illustrative purposes only and are not intended to represent any physical feature of the shoulder 155 or any other part 155 of the patient 160.

In locating the specimen reference points 215a,215b,215c which are typically selected previously for locating, the operator 150 moves the ultrasound transducer 110 to different locations on the shoulder 155 of the patient 160 until the three specimen reference points 215a,215b,215c are found. For ease of illustration and discussion, all three specimen reference points 215a,215b,215c are shown in FIG. 2 as being detected with the ultrasound transducer 110 in a single location, i.e., with the three specimen reference points 215a,215b,215c in a single reference propagation plane 220a. In the more general case, however, as long as current locations of the ultrasound transducer 110 are known relative to a previous location, detection of the three specimen reference points 215a,215b,215c in separate propagation planes 220, i.e., with the ultrasound transducer 110 in separate locations relative to the patient 160 can be used to specify the reference propagation plane 220a.

Also shown in FIG. 2 are three transducer targets 230 (first transducer target 230a, second transducer target 230b, and third transducer target 230c) and three specimen targets 240 (first specimen target 240a, second specimen target 240b, and third specimen target 240c). In representative embodiments, the emitter device 196 of the location detection unit 190 transmits one or more location interrogation signals 192 which are received by the transducer targets 230 and the specimen targets 240. In response to the location interrogation signals 192, the transducer targets 230 and the specimen targets 240 return location information signals 193 which are received by the receptor device 197. The location identification module 195 monitors any movement of the ultrasound transducer 110 and of the patient 160. The location identification module 195 transfers information regarding the locations of the ultrasound transducer 110 and the organic specimen 160 via location data 194 to the processor 130. The transducer and specimen targets 230,240 could transmit location information signals 193 in response to location interrogation signals 192, actively transmit location information signals 193 automatically without initiation from the location interrogation signals 192, or passively reflect the location interrogation signals 192 as location information signals 193. The location interrogation signals 192 and location information signals 193 could be infrared, optical, radio frequency or any other acceptable signal types. In addition, information regarding the relative locations of the ultrasound transducer 110 and the organic specimen 160 can be maintained as the ultrasound transducer 110 and/or the organic specimen 160 are/is moved by a mechanical fixture (see FIG. 3) attached to the ultrasound transducer 110 or by an inertial reference device (see FIG. 4) attached to the ultrasound transducer 110.

Figure 3:
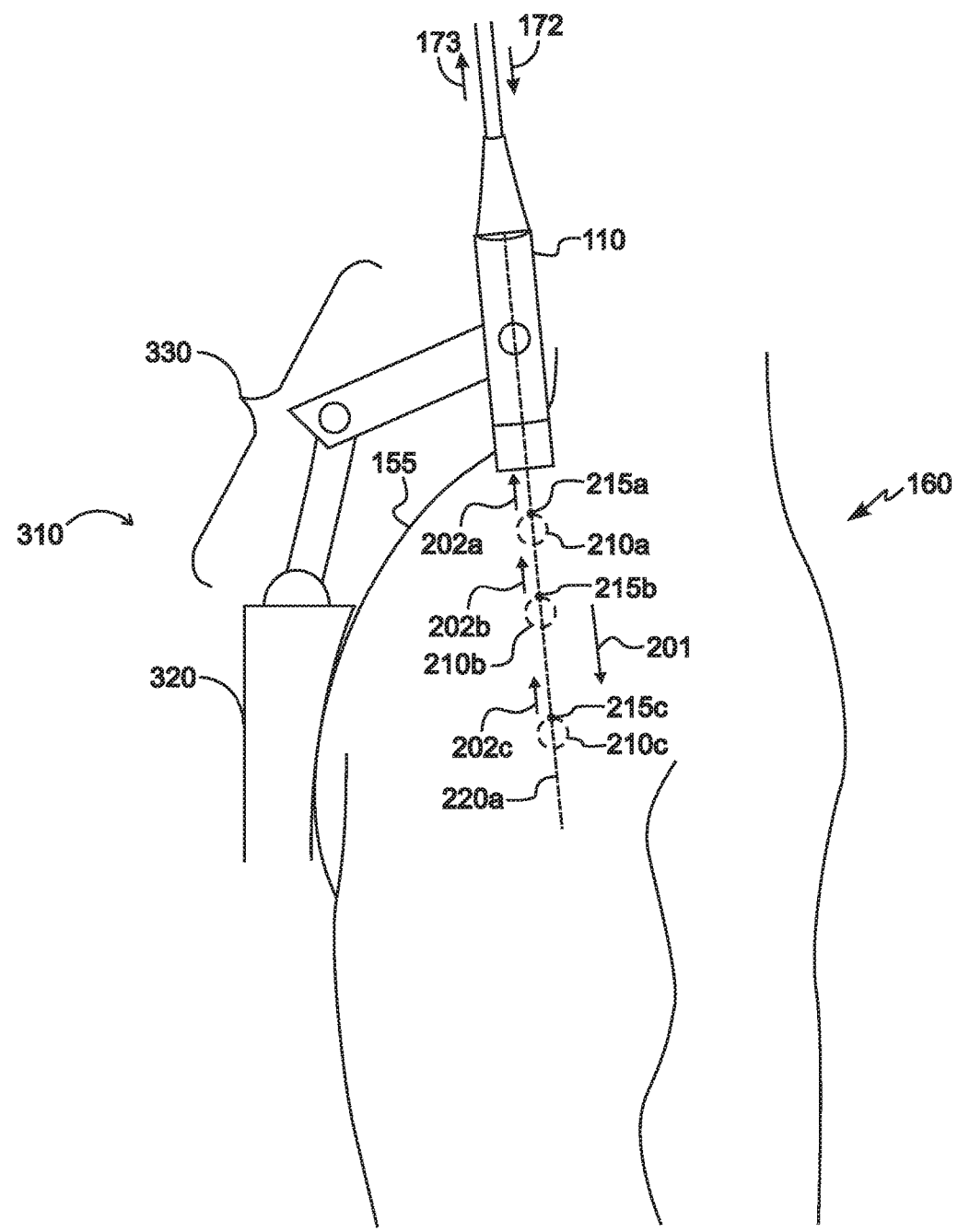
FIG. 3 is a side view of the arrangement whose front view is shown in FIG. 2.

FIG. 3 is a side view of the arrangement whose front view is shown in FIG. 2. As indicated in the discussion of FIG. 2, the three specimen features 210a,210b,210c separately reflect that part of the ultrasound incident wave 201 incident on them as associated ultrasound reflected waves 202a,202b, 202c (first ultrasound reflected wave 202a, second ultrasound reflected wave 202b, and third ultrasound reflected wave 202c). In the representative embodiment of FIGS. 2 and 3, these three specimen features 210a,210b,210c have separately identifiable specimen reference points 215a,215b, 215c that together specify a reference propagation plane 220a that will be used for specifying the location of and identification of additional, detected specimen features 210. The reference propagation plane 220a of the ultrasound incident wave 201 is shown edge on in FIG. 3 and therefore appears as a line in that figure. As previously indicated, all three specimen reference points 215a,215b,215c may be detected with the ultrasound transducer 110 in a single location as shown in FIGS. 2 and 3. However, as long as any current location of the ultrasound transducer 110 is known relative to a previous location, the three specimen reference points 215a,215b,215c can be detected in separate propagation planes 220, i.e., with the ultrasound transducer 110 in separate locations.

Also, shown in FIG. 3 is a representative embodiment wherein the emitter device 196 and the receptor device 197 of the location detection unit 190 are replaced by a mechanical coupling device 310 which can be used to maintain a reference between the location of the ultrasound transducer 110 and the location of the patient 160. The mechanical coupling device 310 comprises a mechanical fixture 320 and a mechanical coupler 330. In order to reduce or eliminate movement by the patient 160, the mechanical fixture 320 is placed adjacent to the patient 160. The mechanical coupler 330 is located between the mechanical fixture 320 and the ultrasound transducer 110. Measurements of various angular rotations of components in the mechanical coupling device 310 relative to the reference propagation plane 220a can be used to compute the new propagation plane 220 following any movement of the ultrasound transducer 110.

Figure 4:
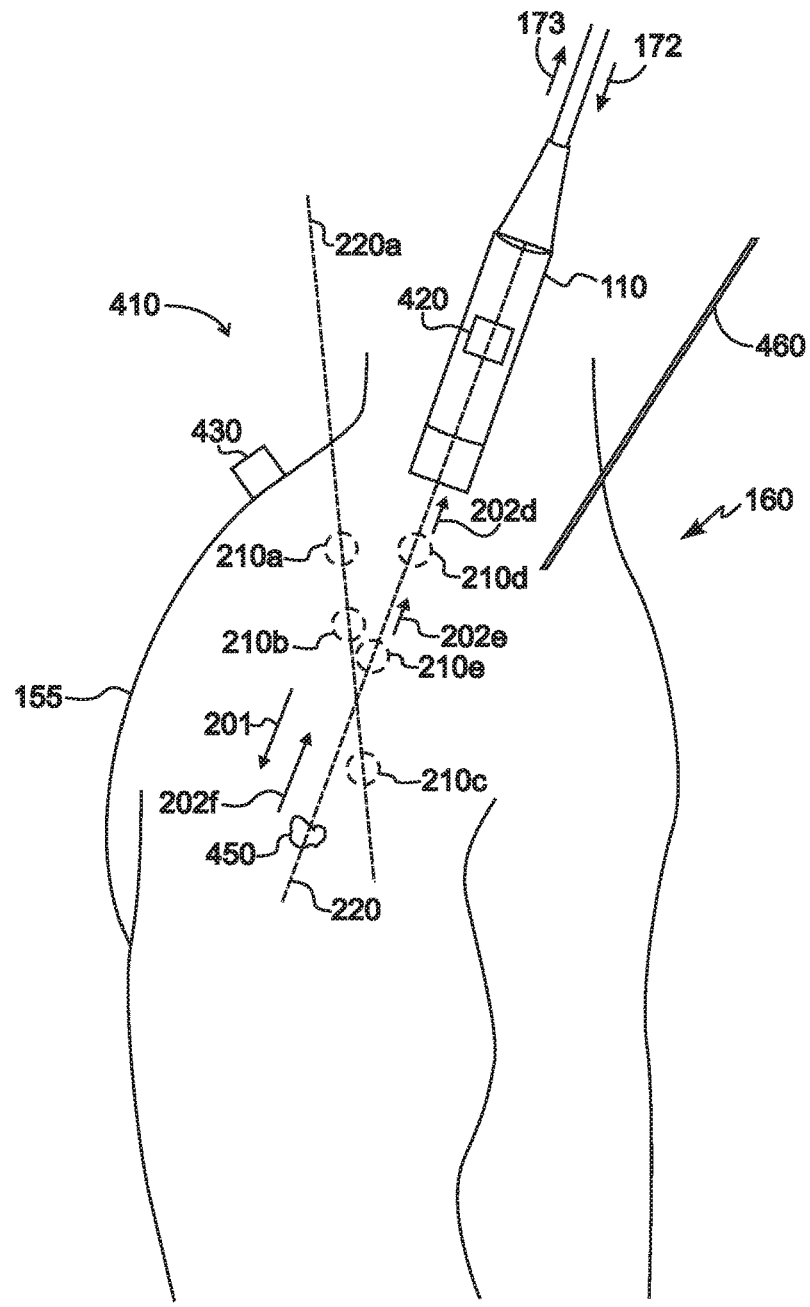
FIG. 4 is a side view of a modified arrangement of the side view shown in FIG. 3.

FIG. 4 is a side view of a modified arrangement of the side view shown in FIG. 3. In FIG. 4, the ultrasound transducer 110 is again coupled to the shoulder 155 of the patient 160. However, the ultrasound transducer 110 has been moved to another location on the shoulder 155 of the patient 160.

Also, shown in FIG. 4 is a representative embodiment wherein the emitter device 196 and the receptor device 197 of the location detection unit 190 of FIGS. 1A, 1B, and 1C are replaced by an inertial reference device 410 which can be used to maintain a reference between the location of the ultrasound transducer 110 and the location of the patient 160. The inertial reference device 410 comprises a first inertial module 420 and a second inertial module 430. The first inertial module 420 is coupled to the ultrasound transducer 110 and a second inertial module 430 is coupled to the patient 160. Communication between the first and the second inertial modules 420,430 and the processor 130 can be effected by infrared, optical, radio frequency, or any other acceptable communication technology. A combination of the mechanical fixture 320 in FIG. 3 coupled to the patient 160 and the first inertial module 420 coupled to the ultrasound transducer 110 can also be used to maintain information regarding the location of the ultrasound transducer 110 relative to the patient 160.

As previously discussed, the ultrasound transducer 110 converts the activation signal 172 to an ultrasound incident wave 201 and transmits it into the shoulder 155 of the patient 160 in the propagation plane 220. The ultrasound incident wave 201 in FIG. 4 is reflected in the patient's shoulder 155 by two additional specimen features 210d,210e (fourth specimen feature 210d and fifth specimen feature 210e) and the patient unique feature 450 as additional ultrasound reflected waves 202d,202e,202f (fourth ultrasound reflected wave 202d, fifth ultrasound reflected wave 202e, and sixth ultrasound reflected wave 202f). The ultrasound reflected waves 202d,202e,202f are detected by the ultrasound transducer 110 and converted into the reflected data signal 173. However, the three specimen features 210a,210b,210c and their associated specimen reference points 215a,215b,215c are not detectable by the ultrasound transducer 110 with the ultrasound transducer 110 positioned as in FIG. 4 as these specimen features 210a,210b,210c do not lie in the current propagation plane 220.

Also in FIG. 4 is an instrument 460 shown inserted into the patient's 160 shoulder 155. The placement of the instrument 460 within the patient's 160 shoulder 155 can be adjusted using appropriate ultrasound transducer 110 positions and the resultant displayed ultrasound and model images 180,185. The instrument 460 can be configured for providing medical treatment to the patient 160 or for obtaining diagnostic information regarding the patient 160 such as obtaining a biopsy.

Figure 5:
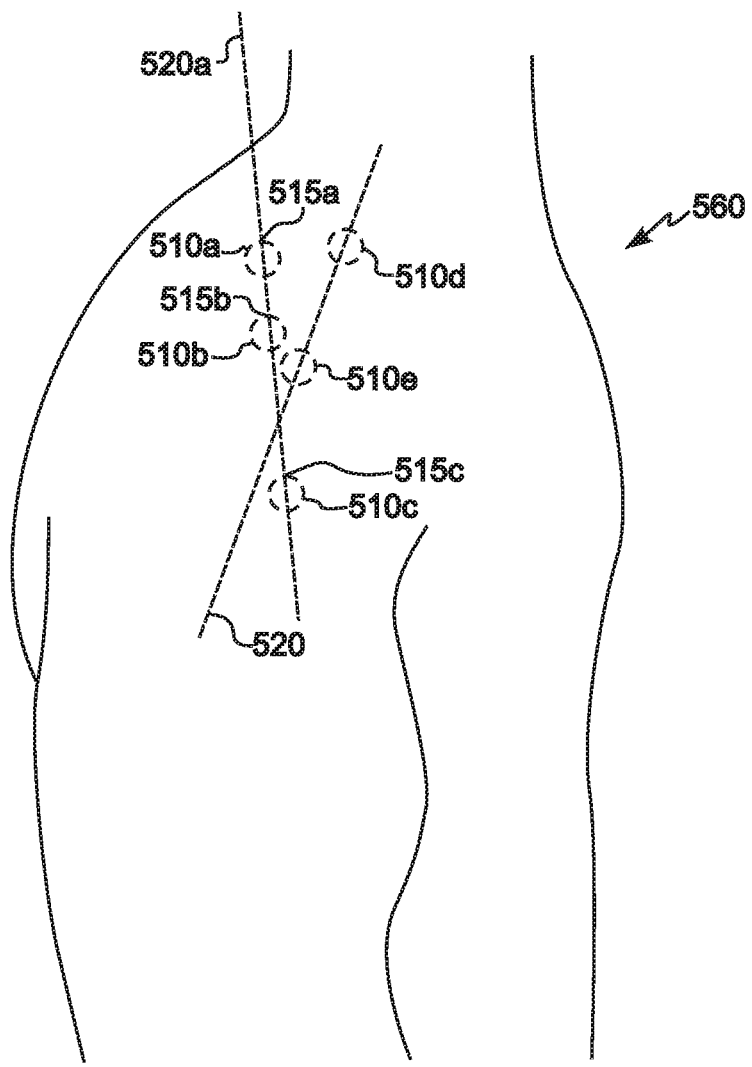
FIG. 5 is a side view of a three-dimensional reconstructed model from the anatomic model data for the arrangement of FIG. 4.

FIG. 5 is a side view of a three-dimensional reconstructed model 560 from the anatomic model data 186 for the arrangement of FIG. 4. In FIG. 5 are shown a first, a second, a third, a fourth, and a fifth model features 510a,510b,510c, 510d,510e that in order correspond to the first, the second, the third, the fourth, and the fifth specimen features 210a, 210b,210c,210d,210e and a first, a second, and a third model reference points 515a,515b,515c that in order correspond to the first, the second, and the third specimen reference points 215a,215b,215c shown in FIG. 4. Also shown in FIG. 5 is a model image plane 520 that corresponds to the propagation plane 220 (the ultrasound image plane 220) of FIG. 4. Note that the first, the second, and the third model features 510a,510b,510c and their associated first, second, and third model reference points 515a,515b,515c lie in another model image plane 520a referred to herein as the reference model image plane 520a. The reference model image plane 520a for the model image 185 that includes the first, second, and third model reference points 515a,515b,515c corresponds to the reference ultrasound image plane 220a for the ultrasound image 180 that includes the first, second, and third specimen reference points 215a,215b,215c. Note also, that FIG. 5 does not include a model feature 510 that corresponds to the patient unique feature 450 as such items are not a part of the anatomic model data 186.

Figure 6:
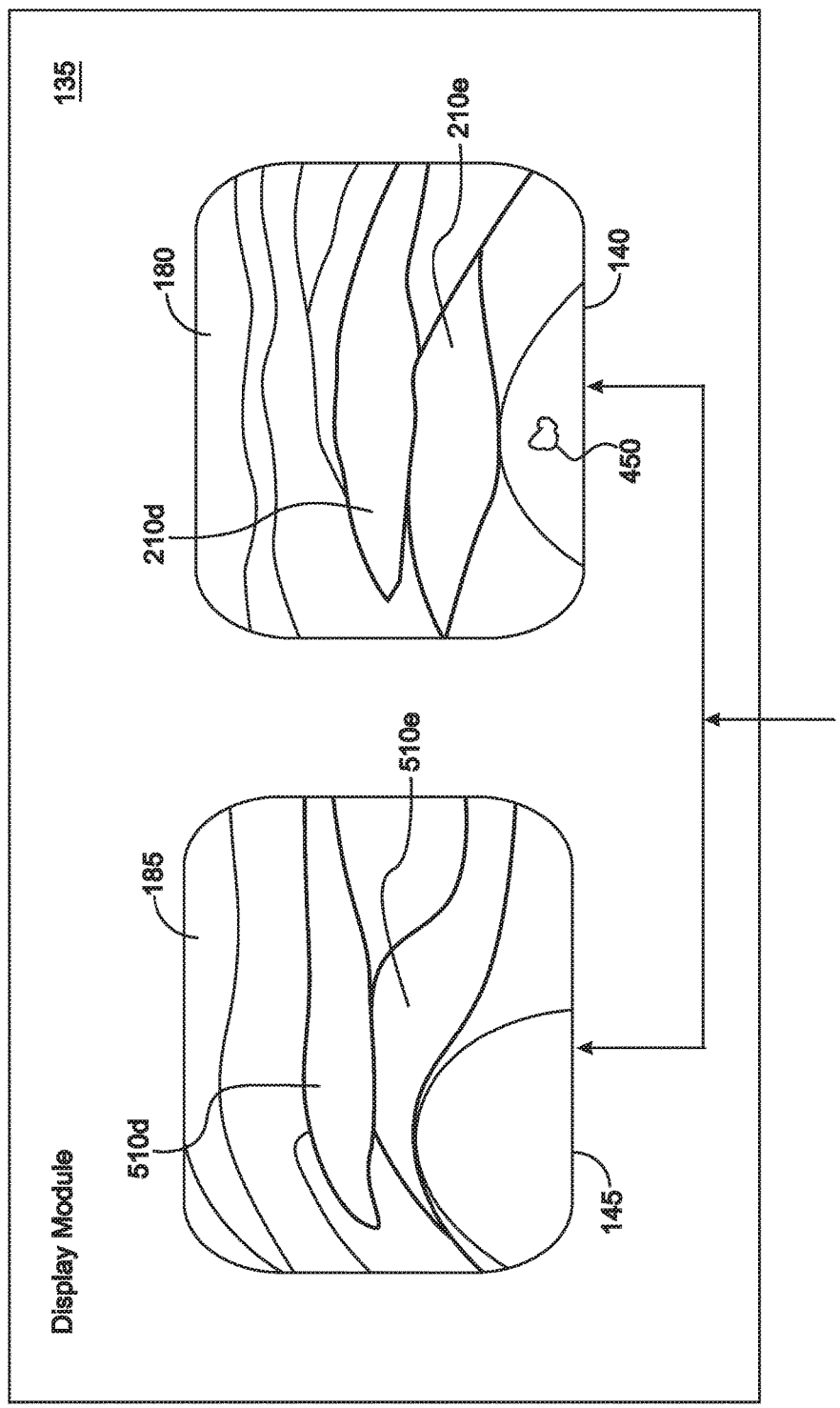
FIG. 6 is another drawing of the display module of FIGS. 1A, 1B, 1C, 1D, 1E, 1F, 1G, 1H and 1I with the ultrasound transducer placed as in FIG. 4.

FIG. 6 is another drawing of the display module 135 of FIGS. 1A, 1B, 1C, 1D, 1E, 1F, 1G, 1H and 1I with the ultrasound transducer 110 placed as in FIG. 4. In FIG. 6, as in FIGS. 1A, 1B, and 1C, the ultrasound image 180 is displayed on the ultrasound display 140 and a corresponding model image 185 is preferably displayed concurrently on the model display 145. The model image 185 is a display of a two-dimensional slice through a representative model of the patient 160 for a plane that corresponds to the propagation plane 220 of the ultrasound incident wave 201 shown in FIG. 4. The ultrasound reflection of the fourth and the fifth specimen features 210d,210e and the patient unique feature 450 of the ultrasound image 180 of the patient's shoulder 155 are indicated on the ultrasound display 140, and the corresponding model features 510 (fourth model feature 510d and fifth model feature 510ec) are shown on the model image 185 displayed on the model display 145.

Other locations of the ultrasound transducer 110 will result in displayed ultrasound and model images 180,185 for other propagation planes 220. A set of ultrasound data 187 for the ultrasound image 180 can be stored for future reference and future creation of ultrasound images 180 in the ultrasound memory 127 of the memory module 125. The stored set of ultrasound data 187 can be keyed to or stored with a set of model extracted data 188 obtained from the anatomic model data 186 for the region of that part 155 of the patient 160 from which the ultrasound data 187 was obtained.

The two specimen features 210d,210e, the patient unique feature 450, and the two model features 510d,510e in FIG. 6 are shown for illustrative purposes only and are not intended to represent any particular feature 210 or patient unique feature 450 in the shoulder 155 or any other part 155 of the patient 160.

Figure 7:
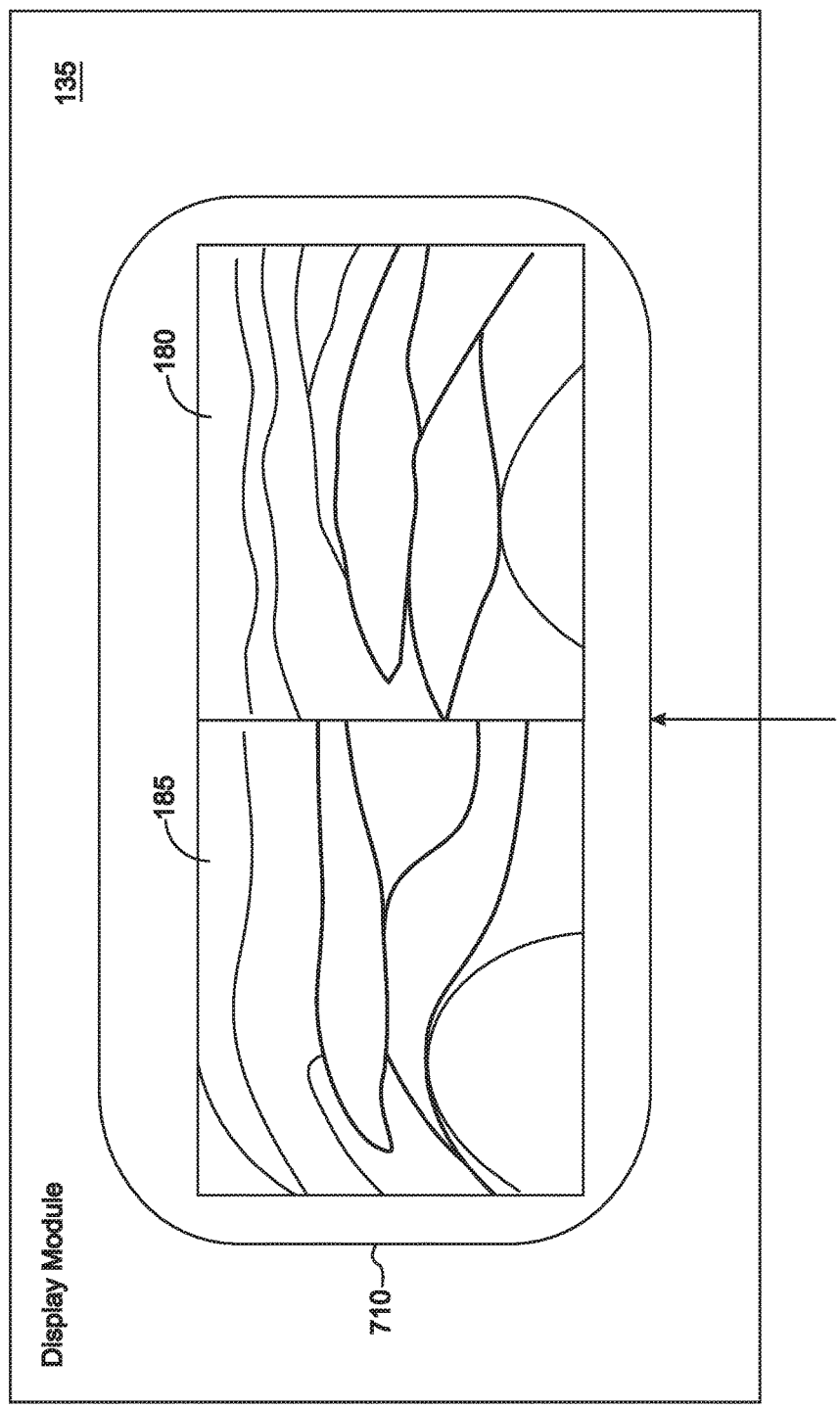
FIG. 7 is a drawing of an alternative embodiment of a display module for the systems of FIGS. 1A, 1B, 1C, 1D, 1E, 1F, 1G, 1H and 1I.

FIG. 7 is a drawing of an alternative embodiment of a display module 135 for the systems 100 of FIGS. 1A, 1B, 1C, 1D, 1E, 1F, 1G, 1H and 1I. The display module 135 of FIG. 7 comprises a single display 710 in a split screen mode for the combined display of the ultrasound image 180 and the model image 185. For ease and clarity of illustration, the two specimen features 210*d*,210*e* and the patient unique feature 450 as well as the corresponding two model features 510*d*,510*e* are not labeled in FIG. 7 as they were in FIG. 6.

As in FIG. 6, other locations of the ultrasound transducer 110 will result in displayed ultrasound and model images 180,185 for other propagation planes 220. A set of ultrasound data 187 for the ultrasound image 180 can be stored for future reference and future creation of ultrasound images 180 in the ultrasound memory 127 of the memory module 125. The stored set of ultrasound data 187 can be keyed to or stored with a set of model extracted data 188 obtained from the anatomic model data 186 for the region of that part 155 of the patient 160 from which the ultrasound data 187 was obtained.

Figure 8:
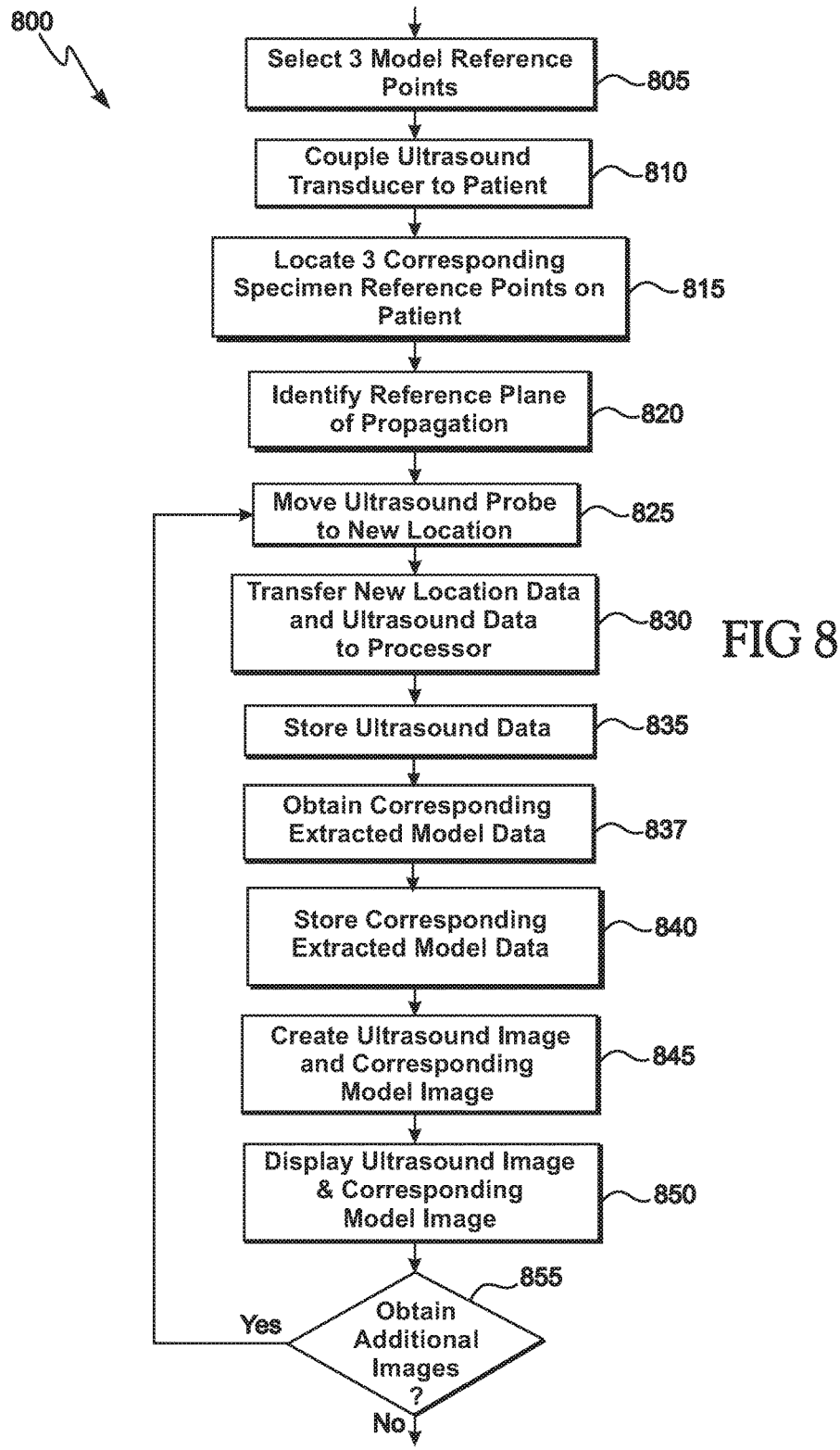
FIG. 8 is a flow chart of a method for the identification of organic specimen features in ultrasound images as described in various representative embodiments.

FIG. 8 is a flow chart of a method 800 for the identification of organic specimen 160 features 210 in ultrasound images 180 as described in various representative embodiments. In block 805 of FIG. 8, three model reference points 515 (first, second, and third model reference points 515*a*, 515*b*,515*c*) are selected. Block 805 then transfers control to block 810.

In block 810, the ultrasound transducer 110 is coupled to the organic specimen 160 which could be, for example, the patient 160. Block 810 then transfers control to block 815.

In block 815, the ultrasound transducer 110 is moved until the three specimen reference points 215 (first, second, and third specimen reference points 215*a*,215*b*,215*c*) on the patient 160 that correspond to the three model reference points 515 (first, second, and third model reference points 515*a*,515*b*,515*c*) are located and marked on the ultrasound data 187. Block 815 then transfers control to block 820.

In block 820, the reference propagation plane 220*a* is identified based on the first, the second, and the third specimen reference points 215*a*,215*b*,215*c*. Block 820 then transfers control to block 825.

In block 825, the ultrasound transducer 110 is moved to a new location on the patient 160. Block 825 then transfers control to block 830.

In block 830, data specifying the new location of the ultrasound transducer 110 is transferred by the location detection unit 190 to the processor 130, and the reflected data signal 173 is transferred to the processor 130 from which a set of ultrasound data 187 is obtained. Block 830 then transfers control to block 835.

In block 835, the set of ultrasound data 187 is stored in the ultrasound memory 127. Block 835 then transfers control to block 837.

In block 837, a set of model extracted data 188 is obtained from the anatomic model data 186 in the anatomic model memory 126 for the region from which the set of ultrasound data 187 is obtained. Block 837 then transfers control to block 840.

In block 840, the corresponding set of model extracted data 188 is stored in the extracted model memory 128. Block 840 then transfers control to block 845.

In block 845, an ultrasound image 180 is created from the set of ultrasound data 187, and a corresponding model image 185 is created from the associated set of model extracted data 188. Block 845 then transfers control to block 850.

In block 850, the ultrasound image 180 and the corresponding model image 185 are displayed on the display module 135. Block 850 then transfers control to block 855.

In block 855, if an additional ultrasound image 180 and corresponding model image 185 are to be obtained, block 855 transfers control back to block 825. Otherwise, block 855 terminates the process.

Figure 9:
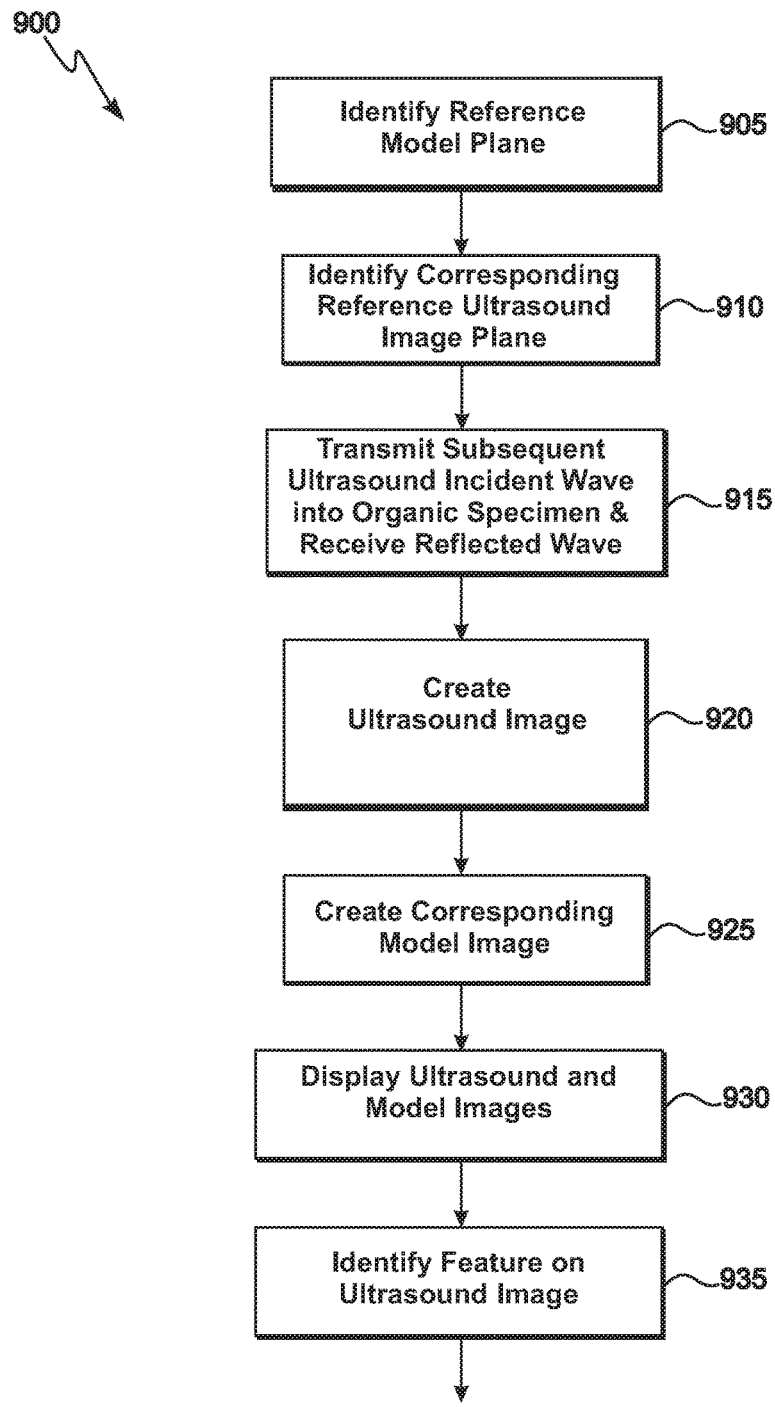
FIG. 9 is a flow chart of another method for the identification of organic specimen features in ultrasound images as described in various representative embodiments.

FIG. 9 is a flow chart of another method 900 for the identification of organic specimen 160 features 210 in ultrasound images 180 as described in various representative embodiments. In block 905 of FIG. 9, a reference model image plane 520*a* in anatomic model data 186 of at least a part 155 of an organic specimen 160 is identified. Block 905 then transfers control to block 910.

In block 910, a corresponding reference ultrasound image plane 220*a* is identified by transmitting one or more ultrasound incident waves 201 into the organic specimen 160 and receiving corresponding one or more ultrasound reflected waves 202. Positional awareness is maintained between the one or more ultrasound reflected waves 202. Block 910 then transfers control to block 915.

In block 915, at least one subsequent ultrasound incident wave 201 is transmitted into the organic specimen 160 and at least one corresponding subsequent ultrasound reflected wave 202 reflected from one or more specimen features 210 in the organic specimen 160 is received. Positional awareness is maintained between the reference ultrasound plane 220*a* and a propagation plane 220 of the at least one subsequent ultrasound incident wave 201. Block 915 then transfers control to block 920.

In block 920, for at least one subsequent ultrasound reflected wave 202, an ultrasound image 180, is created therefrom. Block 920 then transfers control to block 925.

In block 925, for the at least one subsequent ultrasound reflected wave 202, a corresponding model image 185 from the anatomic model data 186 for the model image plane 520 that corresponds to the ultrasound image plane 220 for the at least one subsequent ultrasound reflected wave 202 is created. Block 925 then transfers control to block 930.

In block 930, for the at least one subsequent ultrasound reflected wave 202, the ultrasound image 180 and the model image 185 are displayed on a display module 135. Block 930 then transfers control to block 935.

In block 935, for the at least one subsequent ultrasound reflected wave 202, a specimen feature 210 on the ultrasound image 180 is identified from a corresponding model feature 510 on the model image 185. Block 935 then terminates the process.

FIG. 10 is a flow chart of a segment of a method 1000 for the identification of organic specimen features 210 in ultrasound data 187 using a client computer 132-C and a server computer 132-S as described in various representative embodiments. In block 1005 of FIG. 10, a set of one or more ultrasound incident waves 201 are transmitted into an organic specimen 160. Block 1005 then transfers control to block 1010.

In block 1010, a set of one or more location interrogation signals 192 are transmitted to locate the ultrasound transducer 110 relative to the organic specimen 160. Positional awareness between each of the set of one or more ultrasound reflected waves 202 received by the ultrasound transducer 110 can be maintained via the results of each of the set of the one or more additional interrogation signals 192. Block 1010 then transfers control to block 1015.

In block 1015, a set of one or more reflected data signals 173 obtained from a set of one or more ultrasound reflected waves 202 responsive to the set of one or more ultrasound incident waves 201 transmitted into the organic specimen 160 are received back from the organic specimen 160. Block 1015 then transfers control to block 1020.

In block 1020, a set of one or more location information signals 193 responsive to the set of transmitted one or more location interrogation signals 192 are received back from transducer targets 230 and specimen targets 240. Block 1020 then transfers control to block 1025.

In block 1025, the set of one or more reflected data signals 173 are transferred to the client computer 132-C. Block 1025 then transfers control to block 1030.

In block 1030, the set of one or more location information signals 193 are transferred to the client computer 132-C. Block 1030 then transfers control to block 1035.

In block 1035, the set of one or more reflected data signals 173 are appropriately tagged or otherwise labeled such that the set of one or more reflected data signals 173 can be associated with the set of one or more location information signals 193. The various tags could comprise date-time stamps using the clock of the client computer 132-C. Block 1035 then transfers control to block 1040.

In block 1040, the set of one or more location information signals 193 are appropriately tagged or otherwise labeled such that the set of one or more reflected data signals 173 can be associated with the set of one or more location information signals 193. The various tags could comprise date-time stamps using the clock of the client computer 132-C. Block 1040 then transfers control to block 1045.

In block 1045, the set of one or more reflected data signals 173 are transferred to the server computer 132-S. Block 1045 then transfers control to block 1050.

In block 1050, the set of one or more location information signals 193 are transferred to the server computer 132-S. Block 1050 then transfers control to block 1055.

In block 1055, a reference model image region 520a in anatomic model data 186 of at least a part 155 of an organic specimen 160 and a corresponding reference ultrasound image region 220a are identified from the set of one or more reflected data signals 173 and the set of one or more location information signals 193 that were transferred to the server computer 132-S. Positional awareness was maintained between each of the set of one or more ultrasound reflected waves 202 received by the ultrasound transducer 110. This positional awareness of the reflected data signals 173 could have been maintained by pairing each of the one or more reflected data signals 173 with its corresponding location information signal 193 by, for example, inspecting the tags such as date-time stamps on each signal with the appropriate coupling of each of the set of reflected data signals 173 and corresponding location information signal 193. The correlation of the ultrasound data 187 from the reflected data signals 173 and the anatomic model data 186 to determine a reference model image region 520a and a reference ultrasound image region 220a could be performed automatically by the correlation logic module 105. Block 1055 can then transfer control to Block 1105 of FIG. 11 or can optionally transfer control to Block 1205 of FIG. 12.

FIG. 11 is a flow chart of another segment of a method 1100 for the identification of organic specimen features 210 in ultrasound data 187 using a client computer 132-C and a server computer 132-S as described in various representative embodiments. In block 1105 of FIG. 11, a set of one or more additional ultrasound incident waves 201 are transmitted into the organic specimen 160. Block 1105 then transfers control to block 1110.

In block 1110, a set of one or more additional location interrogation signals 192 are transmitted to locate the ultrasound transducer 110 relative to the organic specimen 160. Positional awareness between each of the set of one or more additional ultrasound reflected waves 202 received by the ultrasound transducer 110 can be maintained via the results of each of the set of the one or more additional interrogation signals 192. Block 1110 then transfers control to block 1115.

In block 1115, a set of one or more additional reflected data signals 173 obtained from the set of one or more additional ultrasound reflected waves 202 responsive to the set of one or more additional ultrasound incident waves 201 transmitted into the organic specimen 160 are received back from the organic specimen 160. Block 1115 then transfers control to block 1120.

In block 1120, a set of one or more additional location information signals 193 responsive to the transmitted set of the set of one or more additional location interrogation signals 192 are received back from transducer targets 230 and specimen targets 240. Block 1120 then transfers control to block 1125.

In block 1125, the set of one or more additional reflected data signals 173 are transferred to the client computer 132-C. Block 1125 then transfers control to block 1130.

In block 1130, the set of one or more additional location information signals 193 are transferred to the client computer 132-C. Block 1130 then transfers control to block 1135.

In block 1135, the set of one or more additional reflected data signals 173 are appropriately tagged or otherwise labeled such that the one or more additional reflected data signals 173 can be associated with the set of one or more additional location information signals 193. The various tags could comprise date-time stamps using the clock of the client computer 132-C. Block 1135 then transfers control to block 1140.

In block 1140, the set of one or more additional location information signals 193 are appropriately tagged or otherwise labeled such that the one or more additional reflected data signals 173 can be associated with the set of one or more additional location information signals 193. The various tags could comprise date-time stamps using the clock of the client computer 132-C. Block 1140 then transfers control to block 1145.

In block 1145, the set of one or more additional reflected data signals 173 are transferred to the server computer 132-S. Block 1145 then transfers control to block 1150.

In block 1150, the set of one or more additional location information signals 193 are transferred to the server computer 132-S. Block 1150 then transfers control to block 1155.

In block 1155, a reference model image region 520a in anatomic model data 186 of at least a part 155 of an organic specimen 160 and a corresponding reference ultrasound image plane 220a are identified from the set of one or more additional reflected data signals 173 and the one or more additional location information signals 193 that were transferred to the server computer 132-S. Positional awareness was maintained between the one or more additional ultrasound reflected waves 202 received by the ultrasound transducer 110 as well as the reference propagation region 220. This positional awareness of the additional reflected data signals 173 could have been maintained by pairing each of the one or more additional reflected data signals 173 with its corresponding additional location information signal 193 by, for example, inspecting the tags such as date-time stamps on each signal with the appropriate coupling of the additional reflected data signals 173 and the corresponding additional location information signal 193. The correlation of the ultrasound data 187 from the reflected data signals 173 and the anatomic model data 186 to determine a model image region 520a and a corresponding ultrasound image region 220*a* could be performed automatically by the correlation logic module 105. Block 1155 can then transfer control to Block 1205 of FIG. 12.

FIG. 12 is a flow chart of still another segment of a method 1200 for the identification of organic specimen features 210 in ultrasound data 187 using a client computer 132-C and a server computer 132-S as described in various representative embodiments. The descriptor "image" as used herein generally describes a data set or data stream which is representative of at least a portion of a model of an organic specimen or as found in or from data of ultrasound data obtained from the organic specimen. It may, but is not limited to, a data set representative of at least a part of a visual image of the organic specimen or model thereof. The steps of the still another method segment 1200 of FIG. 12 are applicable to any sets of one or more ultrasound image data 180 and/or sets of one or more model image data 185 including sets of one or more reference ultrasound image data 180, sets of one or more reference model image data 185, sets of one or more additional ultrasound image data 180, and/or sets of one or more model image data 185.

In block 1205, ultrasound image data 180 is created from the set of ultrasound data 187, and corresponding, associated model image data 185 is created from the associated set of model extracted data 188. Block 1205 then transfers control to block 1210.

In block 1210, optionally one or more ultrasound images 180 and/or one or more model images 185 can be displayed on the server display module 135-S. Block 1210 then transfers control to block 1215.

In block 1215, ultrasound image data 180 and corresponding, associated model image data 185 from the associated set of model extracted data 188 are analyzed. Such analysis could be performed using model image data 185 from one or more sources such as, for example, the Visible Human Project® (VHP), MRI data, X-Ray data, other ultrasound data, or any other appropriate source. The analysis could also be performed automatically by the server processor. Block 1215 then transfers control to block 1220.

In block 1220, optionally a message 170 is created and transferred to the client computer 132-C. The message 170 could also be transferred via cell phones or other appropriate communication device as, for example, a voice or text message—digital or analogue. This message 170 could, for example, request an action by the operator such as a move to a designated region of the organic specimen 160. Block 1220 then transfers control to block 1225.

In block 1225, ultrasound image data 180 and/or model image data 185 are transferred to the client computer 132-C. Block 1225 then transfers control to block 1230.

In block 1230, optionally an ultrasound image 180 and/or a model image 185 can be displayed on the client display module 135-C. Block 1230 can then terminate the process or reinitiate the steps of FIG. 11 at block 1105.

While the representative embodiments disclosed herein have been discussed in terms of the ultrasound transducer 110 coupled to the shoulder 155 of a human patient 160, it will be understood by one of ordinary skill in the art that other representative embodiments can be implemented for use with other parts 155 of any organic specimen 160. As stated above, an organic specimen 160 is any living or deceased organism or any portion of a living or deceased organism. In particular, the organic specimen could be a human, another animal, a plant, or a portion of a human, another animal, or a plant.

In representative embodiments, the ultrasound images 180 and/or the model images 185 could be stored in the memory module 125.

In alternative representative embodiments, the ultrasound controller 120 could be implemented in hardware, as a software program, or in firmware either external to or internal to the processor 130 or either external to or internal to the client processor 130-C as appropriate, In alternative representative embodiments, the location identification module 195 could be implemented in hardware, as a software program, or in firmware either external to or internal to the processor 130 or either external to or internal to the client processor 130-C as appropriate In other representative embodiments, the propagation plane 220 could be adjusted electronically rather than by a physical movement of the ultrasound transducer 110 relative to the organic specimen 160.

The term region as used herein refers to a plane or slice for two-dimensional embodiments and to a volume for three-dimensional embodiments. Generally for both two-dimensional and three-dimensional embodiments, the propagation plane 220 is referred to as the propagation region 220, the ultrasound image plane 220 is referred to as the ultrasound image region 220, the reference propagation plane 220*a* is referred to as the reference propagation region 220*a*, and the reference ultrasound image plane 220*a* is referred to as the reference ultrasound image region 220*a*. Also generally for both two-dimensional and three-dimensional embodiments, the model image plane 520 and the reference model image plane 520*a* are referred to respectively as the model image region 520 and the reference model region 520*a*.

The anatomic model data 186 could be obtained from data sets such as or similar to the Visible Human Project® (VHP) which can be used to create model images 185 of a representative human body (male or female) at diverse selected depths and angular orientations. The anatomic model data 186 could also be based on a theoretical model of an organic specimen 160. The anatomic model data 186 stored in the memory module 125 can be anatomic model data 186 of at least part 155 of the organic specimen 160. The processor 130 could be a central processing unit (CPU) 130 and could be located in a computer. The memory module 125 could be a computer memory 125.

In addition, while representative embodiments herein have been discussed in terms of creating and displaying static, two-dimensional ultrasound images 180, the ultrasound images 180 could also be static, three-dimensional ultrasound images 180, time varying, two-dimensional ultrasound images 180, and time varying, three-dimensional ultrasound images 180. Further, while representative embodiments herein have been discussed in terms of creating and displaying corresponding static, two-dimensional model images 185, the corresponding model images 185 could also be static, three-dimensional model images 185, time varying, two-dimensional model images 185, and time varying, three-dimensional model images 185.

Also, while representative embodiments disclosed herein have been discussed in terms of the various modules, components, and functions being located on or operatively coupled to a single processor 130, multiple processors 130 can instead be employed. And further, while representative embodiments disclosed herein have been discussed in terms of the various modules, components, and functions being located locally, at least one of these can instead be distributed.

In a first representative embodiment, a system is disclosed. The system comprises an ultrasound transducer 110 configured for transmitting ultrasound incident waves 201 into selected regions 220 of an organic specimen 160, detecting resultant ultrasound reflected waves 202 from specimen features 210 of the organic specimen 160, and transferring ultrasound data 187 in the resultant ultrasound reflected waves 202 for each of multiple selected ultrasound incident waves 201 to a processor 130; a location detection unit 190 configured for detecting locations of the ultrasound transducer 110 and the organic specimen 160 and for transferring that location data 194 to the processor 130; a memory module 125 configured for storing anatomic model data 186 for at least part 155 of the organic specimen 160; the processor 130 configured for identifying the region 220 associated with selected ultrasound data 187 using location data 194 and one or more sets of ultrasound data 187 resultant from reflections of recognized specimen features 210, creating an ultrasound image 180 from the selected ultrasound data 187, obtaining model extracted data 188 from the anatomic model data 186 corresponding to that of the selected ultrasound data 187 region 220, creating a model image 185 from that model extracted data 188, and transferring the ultrasound image 180 and the model image 185 to a display module 135; and the display module 135 configured for displaying the ultrasound image 180 and the model image 185.

In an optional aspect of the first representative embodiment, wherein the memory module 125 is further configured for storing the model extracted data 188.

In an optional aspect of the first representative embodiment, wherein the memory module 125 is further configured for storing the ultrasound data 187.

In an optional aspect of the first representative embodiment, wherein the processor 130 is configured for creating and the display module 135 is configured for displaying at least one static, two-dimensional ultrasound image 180 and its associated static, two-dimensional model image 185, and/or at least one static, three-dimensional ultrasound image 180 and its associated static, three-dimensional model image 185, and/or at least one set of time varying, two-dimensional ultrasound images 180 and its associated set of time varying, two-dimensional model images 185, and/or at least one set of time varying, three-dimensional ultrasound images 180 and its associated set of time varying, three-dimensional model images 185.

In an optional aspect of the first representative embodiment, wherein the processor 130 is a central processing unit 130.

In an optional aspect of the first representative embodiment, wherein the display module 135 comprises a first display 140 and a second display 145 and wherein the ultrasound image 180 is displayed on the first display 140 and the model image 185 is displayed on the second display 145.

In an optional aspect of the first representative embodiment, wherein the ultrasound image 180 and the model image 185 are overlaid on the display module 135 or wherein the ultrasound image 180 and the model image 185 are displayed side-by-side on the display module 135.

In an optional aspect of the first representative embodiment, wherein the model image 185 and the ultrasound image 180 are scaled to each other.

In an optional aspect of the first representative embodiment, wherein the anatomic model data 186 is obtained from the Visible Human Project data 186 for a representative human male or a representative human female.

In an optional aspect of the first representative embodiment, wherein the anatomic model data 186 is of a representative human male or a representative human female.

In an optional aspect of the first representative embodiment, wherein the resultant ultrasound reflected wave 202 further comprises reflections from a patient unique feature 450 in the organic specimen 160.

In an optional aspect of the first representative embodiment, wherein the resultant ultrasound reflected wave 202 further comprises reflections from an instrument 460 inserted into the organic specimen 160 when the ultrasound transducer 110 is appropriately located.

In an optional aspect of the first representative embodiment, wherein the resultant ultrasound reflected wave 202 further comprises reflections from an instrument 460 inserted into the organic specimen 160 when the ultrasound transducer 110 is appropriately located and wherein the instrument 460 is configured for providing medical treatment to the organic specimen 160 or is configured for providing diagnostic information regarding the organic specimen 160.

In a second representative embodiment, a method is disclosed. The method comprises specifying a reference model image region 520*a* in model extracted data 188 obtained from anatomic model data 186 of at least part 155 of an organic specimen 160; transmitting ultrasound incident waves 201 into the organic specimen 160 and receiving thereby ultrasound data 187 from ultrasound reflected waves 202 from specimen features 210 in the organic specimen 160, wherein positional awareness 194 of each ultrasound reflected wave 202 relative to the organic specimen 160 is maintained; identifying a reference propagation region 220*a* corresponding to the reference model image region 520*a* from paired recognized specimen features 210 in the ultrasound data 187 and in the model extracted data 188; transmitting at least one subsequent ultrasound incident wave 201 into the organic specimen 160 and receiving thereby subsequent ultrasound data 187 from ultrasound reflected waves 202 from one or more specimen features 210, wherein positional awareness is maintained between the reference propagation region 220*a* and the propagation region 220 of the subsequent ultrasound data 187; and for the subsequent ultrasound data 187, creating an ultrasound image 180, creating a model image 185 for a model image region 520 from the anatomic model data 186 corresponding to the propagation region 220 of the subsequent ultrasound data 187, and displaying the ultrasound image 180 and the model image 185 on a display module 135.

In an optional aspect of the second representative embodiment, the method 900 further comprises identifying at least one specimen feature 210 on the ultrasound image 180 from a corresponding model feature 510 on the model image 185.

In an optional aspect of the second representative embodiment, wherein the reference model image region 520*a* is a plane 520*a* and is specified by three non-collinear model reference points 515*a*,515*b*,515*c* in the anatomic model data 186 of at least part 155 of the organic specimen 160.

In an optional aspect of the second representative embodiment, wherein the reference model image region 520*a* is a plane 520*a* and is specified by three non-collinear model reference points 515*a*,515*b*,515*c* in the anatomic model data 186 of at least part 155 of the organic specimen 160 and wherein the reference propagation region 220*a* in the organic specimen 160 is a plane 220*a* corresponding to the reference model image plane 520*a* and is identified when one or more ultrasound incident waves 201 are reflected separately or in combination from three specimen reference points 215a,215b,215c corresponding to the three model reference points 515a,515b,515c.

In an optional aspect of the second representative embodiment, wherein the model extracted data 188 is stored in a memory module 125.

In an optional aspect of the second representative embodiment, wherein the ultrasound data 187 is stored in a memory module 125.

In an optional aspect of the second representative embodiment, wherein displaying the ultrasound image 180 and the model image 185 on the display module 135 comprises: displaying at least one static, two-dimensional ultrasound image 180 and its associated static, two-dimensional model image 185, and/or displaying at least one static, three-dimensional ultrasound image 180 and its associated static, three-dimensional model image 185, and/or displaying at least one set of time varying, two-dimensional ultrasound images 180 and its associated set of time varying, two-dimensional model images 185, and/or displaying at least one set of time varying, three-dimensional ultrasound images 180 and its associated set of time varying, three-dimensional model images 185.

In an optional aspect of the second representative embodiment, wherein the anatomic model data 186 is stored in a memory module 125.

In an optional aspect of the second representative embodiment, wherein the display module 135 comprises a first display 140 and a second display 145 and wherein the ultrasound image 180 is displayed on the first display 140 and the model image 185 is displayed on the second display 145.

In an optional aspect of the second representative embodiment, wherein the ultrasound image 180 and the model image 185 are overlaid on the display module 135 or wherein the ultrasound image 180 and the model image 185 are displayed side-by-side on the display module 135.

In an optional aspect of the second representative embodiment, wherein the model image 185 and the ultrasound image 180 are scaled to each other.

In an optional aspect of the second representative embodiment, wherein the anatomic model data 186 is obtained from the Visible Human Project data 186 for a representative human male or a representative human female.

In an optional aspect of the second representative embodiment, wherein the anatomic model data 186 is for a representative human male or a representative human female.

In an optional aspect of the second representative embodiment, further comprising: detecting a patient unique feature 450 in the organic specimen 160.

In an optional aspect of the second representative embodiment, further comprising: inserting an instrument 460 into the organic specimen 160; and adjusting the instrument 460 position within the organic specimen 160 using the displayed ultrasound image 180 and displayed model image 185.

In an optional aspect of the second representative embodiment, further comprising: inserting an instrument 460 into the organic specimen 160; and adjusting the instrument 460 position within the organic specimen 160 using the displayed ultrasound image 180 and displayed model image 185, wherein the instrument 460 is configured for providing medical treatment to the organic specimen 160 or is configured for providing diagnostic information regarding the organic specimen 160.

In a third representative embodiment, a means 100 for identification of an organic specimen 160 feature 210 in an ultrasound image 180 is disclosed. The means comprises an ultrasound means 110 for transmitting ultrasound incident waves 201 into selected regions 210 of an organic specimen 160, detecting resultant ultrasound reflected waves 202 from specimen features 210 of the organic specimen 160, and transferring ultrasound data 187 in the resultant ultrasound reflected waves 202 for each of multiple selected ultrasound incident waves 201 to a processor means 130; a location detection means 190 for detecting locations of the ultrasound means 110 and the organic specimen 160 and for transferring that location data 194 to the processor means 130; a memory means 125 for storing anatomic model data 186 for at least part 155 of the organic specimen 160; the processor means 130 for identifying a region 220 of the organic specimen 160 associated with selected ultrasound data 187 using location data 194 and one or more sets of ultrasound data 187 resultant from reflections of recognized specimen features 210, creating an ultrasound image 180 from the selected ultrasound data 187, obtaining model extracted data 188 from the anatomic model data 186 corresponding to that of the selected ultrasound data 187 region 220, creating a model image 185 from the model extracted data 188, and transferring the ultrasound image 180 and the model image 185 to a display means 135; and the display means 135 configured for displaying the ultrasound image 180 and the model image 185.

In a fourth representative embodiment, a computer program product 133 stored on a non-transitory computer readable storage medium for carrying out a method 900 when executed on a computer 132 is disclosed. The method 900 comprises specifying a reference model image region 520a in model extracted data 188 obtained from anatomic model data 186 of at least part 155 of an organic specimen 160; instructing an ultrasound transducer 110 to transmit ultrasound incident waves 201 into the organic specimen 160 and receiving thereby ultrasound data 187 from ultrasound reflected waves 202 from specimen features 210 in the organic specimen 160, wherein positional awareness 194 of each ultrasound reflected wave 202 relative to the organic specimen 160 is maintained; identifying a reference propagation region 220a corresponding to the reference model image region 520a from paired recognized specimen features 210 in the ultrasound data 202 and in the model extracted data 188; instructing an ultrasound transducer 110 to transmit at least one subsequent ultrasound incident wave 201 into the organic specimen 160 and receiving thereby subsequent ultrasound data 187 from ultrasound reflected waves 202 from one or more specimen features 210, wherein positional awareness is maintained between the reference propagation region 220a and the propagation region 220 of the subsequent ultrasound data 187; and for the subsequent ultrasound data 187, creating an ultrasound image 180, creating a model image 185 for a model image region 520 from the anatomic model data 186 corresponding to the propagation region 220 of the subsequent ultrasound data 187, and instructing a display module 135 to display the ultrasound image 180 and the model image 185.

In an optional aspect of the fourth representative embodiment, the method 900 further comprising: identifying at least one specimen feature 210 on the ultrasound image 180 from a corresponding model feature 510 on the model image 185.

In an optional aspect of the fourth representative embodiment, wherein the reference model image region 520a is a plane 520a and is specified by three non-collinear model reference points 515a,515b,515c in the anatomic model data 186 of at least part 155 of the organic specimen 160.

In an optional aspect of the fourth representative embodiment, wherein the reference model image region 520*a* is a plane 520*a* and is specified by three non-collinear model reference points 515*a*,515*b*,515*c* in the anatomic model data 186 of at least part 155 of the organic specimen 160 and wherein the reference propagation region 220*a* in the organic specimen 160 is a plane 220*a* corresponding to the reference model image plane 520*a* and is identified when one or more ultrasound incident waves 201 are reflected separately or in combination from three specimen reference points 215*a*,215*b*,215*c* corresponding to the three model reference points 515*a*,515*b*,515*c*.

In an optional aspect of the fourth representative embodiment, wherein the model extracted data 188 is stored in a memory module 125.

In an optional aspect of the fourth representative embodiment, wherein the ultrasound data 187 is stored in a memory module 125.

In an optional aspect of the fourth representative embodiment, wherein instructing the display module 135 to display the ultrasound image 180 and the model image 185 comprises: an instruction to display at least one static, two-dimensional ultrasound image 180 and its associated static, two-dimensional model image 185, and/or an instruction to display at least one static, three-dimensional ultrasound image 180 and its associated static, three-dimensional model image 185, and/or an instruction to display at least one set of time varying, two-dimensional ultrasound images 180 and its associated set of time varying, two-dimensional model images 185, and/or an instruction to display at least one set of time varying, three-dimensional ultrasound images 180 and its associated set of time varying, three-dimensional model images 185.

In an optional aspect of the fourth representative embodiment, wherein the anatomic model data 186 is stored in a memory module 125.

In an optional aspect of the fourth representative embodiment, wherein the display module 135 comprises a first display 140 and a second display 145 and wherein the ultrasound image 180 is displayed on the first display 140 and the model image 185 is displayed on the second display 145.

In an optional aspect of the fourth representative embodiment, wherein the ultrasound image 180 and the model image 185 are overlaid on the display module 135 or wherein the ultrasound image 180 and the model image 185 are displayed side-by-side on the display module 135.

In an optional aspect of the fourth representative embodiment, wherein the model image 185 and the ultrasound image 180 are scaled to each other.

In an optional aspect of the fourth representative embodiment, wherein the anatomic model data 186 is obtained from the Visible Human Project data 186 for a representative human male or a representative human female.

In an optional aspect of the fourth representative embodiment, wherein the anatomic model data 186 is for a representative human male or a representative human female.

In an optional aspect of the fourth representative embodiment, the method 900 further comprising: detecting a patient unique feature 450 in the organic specimen 160.

In a fifth representative embodiment, a non-transitory computer-readable medium 125 having computer-executable instructions for causing a computer 132 comprising a processor 130 and associated memory 125 to carry out a method 900 is disclosed. The method 900 comprises specifying a reference model image region 520*a* in model extracted data 188 obtained from anatomic model data 186 of at least part 155 of an organic specimen 160; instructing an ultrasound transducer 110 to transmit ultrasound incident waves 201 into the organic specimen 160 and receiving thereby ultrasound data 187 from ultrasound reflected waves 202 from specimen features 210 in the organic specimen 160, wherein positional awareness 194 of each ultrasound reflected wave 202 relative to the organic specimen 160 is maintained; identifying a reference propagation region 220*a* corresponding to the reference model image region 520*a* from paired recognized specimen features 210 in the ultrasound data 187 and in the model extracted data 188; instructing an ultrasound transducer 110 to transmit at least one subsequent ultrasound incident wave 201 into the organic specimen 160 and receiving thereby subsequent ultrasound data 187 from ultrasound reflected waves 202 from one or more specimen features 210, wherein positional awareness is maintained between the reference propagation region 220*a* and the propagation region 220 of the subsequent ultrasound data 187; and for the subsequent ultrasound data 187, creating an ultrasound image 180, creating a model image 185 for a model image region 520 from the anatomic model data 186 corresponding to the propagation region 220 of the subsequent ultrasound data 187, and instructing a display module 135 to display the ultrasound image 180 and the model image 185.

In a sixth representative embodiment, a system 100 is disclosed. The system 100 comprises a first processor and a first non-volatile memory. The first processor is configured to receive reference ultrasound data 187 from ultrasound reflected waves 202 received from specimen features 210 in an organic specimen 160 resultant from one or more reference ultrasound incident waves 201 transmitted into the organic specimen 160, wherein positional awareness 194 of each ultrasound reflected wave 202 relative to the organic specimen 160 is maintained; to identify a reference propagation region 220*a* in the organic specimen 160 into which at least one of the one or more reference ultrasound incident waves 201 was transmitted into the organic specimen 160 and a corresponding reference model image region 520 in anatomic model data 186, wherein the anatomic model data 186 correspond to at least part of the organic specimen 160; and to receive additional ultrasound data 187 from ultrasound reflected waves 202 received from one or more specimen features 210 in the organic specimen 160 resultant from at least one additional ultrasound incident wave 201 transmitted into the organic specimen 160, wherein positional awareness 194 is maintained between the reference propagation region 220*a* and a propagation region 220 of the additional ultrasound data 187.

In a seventh representative embodiment, a non-transitory computer-readable medium 125 having computer-executable instructions for causing a computer 132 comprising a processor 130 and associated memory 125 to carry out a method 900 is disclosed. The method 900 comprises receiving reference ultrasound data 187 from ultrasound reflected waves 202 received from specimen features 210 in an organic specimen 160 resultant from one or more reference ultrasound incident waves 201 transmitted into the organic specimen 160, wherein positional awareness 194 of each ultrasound reflected wave 202 relative to the organic specimen 160 is maintained; identifying a reference propagation region 220*a* in the organic specimen 160 into which at least one of the one or more reference ultrasound incident waves 201 was transmitted into the organic specimen 160 and a corresponding reference model image region 520 in anatomic model data 186, wherein the anatomic model data 186 correspond to at least part of the organic specimen 160; and receiving additional ultrasound data 187 from ultrasound reflected waves 202 received from one or more specimen features 210 in the organic specimen 160 resultant from at least one additional ultrasound incident wave 201 transmitted into the organic specimen 160, wherein positional awareness 194 is maintained between the reference propagation region 220a and a propagation region 220 of the additional ultrasound data 187.

In representative embodiments, the anatomic model data 186 for at least part of the organic specimen 160 can be for a representative organic specimen, a representative human male, and/or a representative human female that is other than the organic specimen 160 or patient 160 from which ultrasound data 187 is obtained.

It will be appreciated that any module or component disclosed herein that executes instructions may include or otherwise have access to non-transient and tangible computer readable media such as storage media, computer storage media, or data storage devices (removable or non-removable) such as, for example, magnetic disks, optical disks, or tape data storage. Computer storage media may include volatile and non-volatile, removable and non-removable media implemented in any method or technology for storage of information, such as computer readable instructions, data structures, program modules, or other data. Examples of computer storage media include hard drives both internal and external to a computer, RAM, ROM, EEPROM, flash memory or other memory technology, CD-ROM, digital versatile disks (DVD) or other optical storage, USB chips, magnetic cassettes, magnetic tape, magnetic disk storage or other magnetic storage devices, or any other medium which can be used to store the desired information and which can be accessed by an application, module, or both. Any such computer storage media may be part of the server, any component of or related to the network, backend, etc., or accessible or connectable thereto. Any application or module herein described may be implemented using computer readable/executable instructions that may be stored or otherwise held by such computer readable media.

The representative embodiments, which have been described in detail herein, have been presented by way of example and not by way of limitation. It will be understood by those skilled in the art that various changes may be made in the form and details of the described embodiments resulting in equivalent embodiments that remain within the scope of the appended claims.

What is claimed is:

1. A system, comprising:
 a processor, the processor configured
  to receive reference ultrasound data from one or more ultrasound reflected waves reflected from specimen features in an organic specimen resultant from one or more reference ultrasound incident waves transmitted into the organic specimen by an ultrasound transducer,
   wherein positional awareness of each of the one or more reference ultrasound incident waves relative to the organic specimen is maintained using locations of the ultrasound transducer detected by a location detection unit;
  to identify a reference propagation region in the organic specimen and a corresponding reference model region in anatomic model data using specimen feature information in the reference ultrasound data and associated positional awareness information paired with corresponding model feature information in the anatomic model data,
   wherein the anatomic model data correspond to at least part of the organic specimen; and
  to receive additional ultrasound data from an additional ultrasound reflected wave reflected from one or more specimen features in the organic specimen resultant from an additional ultrasound incident wave transmitted into the organic specimen in an additional propagation region by the ultrasound transducer,
   wherein positional awareness is maintained between the reference propagation region and the additional propagation region using locations of the ultrasound transducer detected by the location detection unit.

2. The system as recited in claim 1, further comprising:
 a non-volatile memory,
  wherein the anatomic model data is stored in the non-volatile memory and
  wherein the non-volatile memory is coupled to the processor.

3. The system as recited in claim 1, wherein the reference propagation region, the reference model region, and the additional propagation region are planes.

4. The system as recited in claim 1, the processor further configured
 to identify an additional model region in the anatomic model data corresponding to the additional propagation region using the positional awareness information.

5. The system as recited in claim 4, wherein the reference propagation region, the reference model region, the additional propagation region, and the additional model region are planes.

6. The system as recited in claim 4, the processor further configured
 to identify at least one specimen feature in the ultrasound data of the additional propagation region and its corresponding model feature in the anatomic model data of the additional model region.

7. The system as recited in claim 4, the processor further configured
 to create an ultrasound image using the ultrasound data for the additional propagation region and/or
 to create a model image using the anatomic model data for the additional model region.

8. The system as recited in claim 7, the processor further configured
 to identify at least one specimen feature in the ultrasound image of the additional propagation region and its corresponding model feature in the model image of the additional model region.

9. The system as recited in claim 4, further comprising:
 a display module coupled to the processor,
  wherein the processor is further configured
   to create an ultrasound image using the ultrasound data for the additional propagation region and/or
   to create a model image using the anatomic model data for the additional model region and
   to issue a command to the display module to display the ultrasound image and/or the model image.

10. The system as recited in claim 9, wherein the ultrasound image and the model image displayed on the display module comprise:
 a static, two-dimensional ultrasound image and an associated static, two-dimensional model image, and/or
 a static, three-dimensional ultrasound image and an associated static, three-dimensional model image, and/or a set of time varying, two-dimensional ultrasound images and an associated set of time varying, two-dimensional model images, and/or a set of time varying, three-dimensional ultrasound images and an associated set of time varying, three-dimensional model images.

11. The system as recited in claim 1, wherein the anatomic model data are obtained from at least part of data from a representative human male or a representative human female, and/or from at least part of data from a representative organic specimen that is other than the organic specimen from which the ultrasound data are obtained, and/or from at least part of data from the organic specimen from which the ultrasound data are obtained, and/or from one or more photographs and/or other images and/or other sets of data of one or more physical cross-sections of at least part of the organic specimen or a representative organic specimen.

12. The system as recited in claim 1, wherein the processor is further configured to enable identification in the ultrasound data of a distinctive specimen feature in the organic specimen, and/or an aberrant feature in the organic specimen, and/or an instrument inserted into the organic specimen.

13. The system as recited in claim 1,
wherein the processor is further configured
to correlate ultrasound data from a selected ultrasound reflected wave with corresponding relative location data of the ultrasound transducer maintaining thereby positional awareness of the propagation region of the associated ultrasound incident wave relative to the organic specimen.

14. The system as recited in claim 1, further comprising:
a non-volatile memory,
wherein the processor is a server processor,
wherein the anatomic model data is stored in the non-volatile memory, and
wherein the non-volatile memory is coupled to the server processor.

15. A system, comprising:
a server processor,
wherein the server processor is configured to receive reference ultrasound data via a client processor from one or more ultrasound reflected waves reflected from specimen features in an organic specimen resultant from one or more reference ultrasound incident waves transmitted into the organic specimen,
wherein positional awareness of each of the one or more reference ultrasound incident waves relative to the organic specimen is maintained,
wherein the server processor is configured to identify a reference propagation region in the organic specimen and a corresponding reference model region in anatomic model data using specimen feature information in the reference ultrasound data and associated positional awareness information paired with corresponding model feature information in the anatomic model data,
wherein the anatomic model data correspond to at least part of the organic specimen,
wherein the server processor is configured to receive additional ultrasound data via the client processor from an additional ultrasound reflected wave reflected from one or more specimen features in the organic specimen resultant from an additional ultrasound incident wave transmitted into the organic specimen in an additional propagation region, and
wherein positional awareness is maintained between the reference propagation region and the additional propagation region;
the client processor,
wherein the client processor is coupled to the server processor;
an ultrasound transducer coupled to the client processor, configured to receive the ultrasound reflected waves from specimen features in the organic specimen resultant from the ultrasound incident waves transmitted into the organic specimen by the ultrasound transducer, and configured to transfer the ultrasound data from the ultrasound reflected waves to the client processor; and
a location detection unit coupled to the client processor, configured to detect locations of the ultrasound transducer relative to the organic specimen and configured to transfer the relative location data to the client processor,
wherein the client processor is further configured
to correlate ultrasound data from a selected ultrasound reflected wave with corresponding relative location data of the ultrasound transducer maintaining thereby positional awareness of the propagation region of the associated ultrasound incident wave relative to the organic specimen and to transfer the correlated ultrasound data and relative location data to the server processor or
to transfer the ultrasound data and relative location data to the server processor wherein the server processor is further configured to correlate ultrasound data from a selected ultrasound reflected wave with corresponding relative location data of the ultrasound transducer maintaining thereby positional awareness of the propagation region of the associated ultrasound incident wave relative to the organic specimen.

16. The system as recited in claim 15,
the server processor further configured to create an ultrasound image using ultrasound data for its propagation region and/or a model image using anatomic model data for the associated model region and/or
the client processor further configured to create an ultrasound image using ultrasound data for its propagation region and/or a model image using anatomic model data for the associated model region.

17. The system as recited in claim 16,
the server processor further configured
to identify at least one specimen feature in the ultrasound image and the corresponding model feature in the associated model image; and/or
the client processor further configured
to identify at least one specimen feature in the ultrasound image and its corresponding model feature in the model image.

18. The system as recited in claim 16, further comprising:
a client display module coupled to the client processor and configured to display the ultrasound image and the model image,
wherein the ultrasound image and the model image displayed on the client display module comprise:
a static, two-dimensional ultrasound image and an associated static, two-dimensional model image, and/or a static, three-dimensional ultrasound image and an associated static, three-dimensional model image, and/or a set of time varying, two-dimensional ultrasound images and an associated set of time varying, two-dimensional model images, and/or a set of time varying, three-dimensional ultrasound images and an associated set of time varying, three-dimensional model images.

19. The system as recited in claim 15, the server processor further configured
    to identify at least one specimen feature in the ultrasound data and its corresponding model feature in the anatomic model data; and/or
the client processor further configured
    to identify at least one specimen feature in the ultrasound data and its corresponding model feature in the anatomic model data.

20. The system as recited in claim 15, the server processor further configured to enable identification of a distinctive specimen feature in the organic specimen, and/or an aberrant feature in the organic specimen, and/or an instrument inserted into the organic specimen; and/or the client processor further configured to enable identification of the distinctive specimen feature in the organic specimen, and/or the aberrant feature in the organic specimen, and/or the instrument inserted into the organic specimen.

21. A non-transitory computer-readable medium having computer-executable instructions for causing a computer comprising a processor and associated memory to carry out a method, the method comprising:

receiving reference ultrasound data from one or more ultrasound reflected waves reflected from specimen features in an organic specimen resultant from one or more reference ultrasound incident waves transmitted into the organic specimen by an ultrasound transducer,
    wherein positional awareness of each of the one or more reference ultrasound incident waves relative to the organic specimen is maintained using locations of the ultrasound transducer detected by a location detection unit;

identifying a reference propagation region in the organic specimen and a corresponding reference model region in anatomic model data using specimen feature information in the reference ultrasound data and associated positional awareness information paired with corresponding model feature information in the anatomic model data,
    wherein the anatomic model data correspond to at least part of the organic specimen; and receiving additional ultrasound data from an additional ultrasound reflected wave reflected from one or more specimen features in the organic specimen resultant from an additional ultrasound incident wave transmitted into the organic specimen in an additional propagation region by the ultrasound transducer,
    wherein positional awareness is maintained between the reference propagation region and the additional propagation region using locations of the ultrasound transducer detected by the location detection unit.

22. The non-transitory computer-readable medium as recited in claim 21, wherein the reference propagation region, the reference model region, and the additional propagation region are planes.

23. The non-transitory computer-readable medium as recited in claim 21, the method further comprising:

identifying an additional model region in the anatomic model data corresponding to the additional propagation region using positional awareness information.

24. The non-transitory computer-readable medium as recited in claim 23, wherein the reference propagation region, the reference model region, the additional propagation region, and the additional model region are planes.

25. The non-transitory computer-readable medium as recited in claim 23, the method further comprising:

identifying at least one specimen feature in the ultrasound data of the additional propagation region and its corresponding model feature in the anatomic model data of the additional model region.

26. The non-transitory computer-readable medium as recited in claim 23, the method further comprising:

creating an ultrasound image using the ultrasound data for the additional propagation region and/or creating a model image using the anatomic model data for the additional model region.

27. The non-transitory computer-readable medium as recited in claim 26, the method further comprising:

identifying at least one specimen feature in the ultrasound image of the additional propagation region and its corresponding model feature in the model image of the additional model region.

28. The non-transitory computer-readable medium as recited in claim 26, the method further comprising:

issuing a command to a display module to display the ultrasound image and the model image.

29. The non-transitory computer-readable medium as recited in claim 26, wherein the ultrasound image and the model image comprise:

a static, two-dimensional ultrasound image and an associated static, two-dimensional model image, and/or a static, three-dimensional ultrasound image and an associated static, three-dimensional model image, and/or a set of time varying, two-dimensional ultrasound images and an associated set of time varying, two-dimensional model images, and/or a set of time varying, three-dimensional ultrasound images and an associated set of time varying, three-dimensional model images.

30. The non-transitory computer-readable medium as recited in claim 21, wherein the anatomic model data are obtained from at least part of data from a representative human male or a representative human female, and/or from at least part of data from a representative organic specimen that is other than the organic specimen from which the ultrasound data are obtained, and/or from at least part of data from the organic specimen from which the ultrasound data are obtained, and/or from one or more photographs and/or other images and/or other sets of data of one or more physical cross-sections of at least part of the organic specimen or a representative organic specimen.

31. The non-transitory computer-readable medium as recited in claim 21, the method further comprising:

identifying a distinctive specimen feature in, and/or an aberrant feature in, and/or an instrument inserted into the organic specimen.

32. The non-transitory computer-readable medium as recited in claim 21, wherein the processor and the associated memory are located on a server computer and wherein the ultrasound data and the additional ultrasound data are received via a client computer.

33. The non-transitory computer-readable medium as recited in claim 32,
wherein each of the ultrasound incident waves is transmitted into the organic specimen by an ultrasound transducer and
wherein positional awareness of the propagation region of one or more selected ultrasound incident waves is maintained using location data for the ultrasound transducer relative to the organic specimen.

34. A method for using an ultrasound system, comprising:
receiving reference ultrasound data from one or more ultrasound reflected waves reflected from specimen features in an organic specimen resultant from one or more reference ultrasound incident waves transmitted into the organic specimen by an ultrasound transducer,
wherein positional awareness of each of the one or more reference ultrasound incident waves relative to the organic specimen is maintained using locations of the ultrasound transducer detected by a location detection unit;
identifying a reference propagation region in the organic specimen and a corresponding reference model region in anatomic model data using specimen feature information in the reference ultrasound data and associated positional awareness information paired with corresponding model feature information in the anatomic model data,
wherein the anatomic model data correspond to at least part of the organic specimen; and
receiving additional ultrasound data from an additional ultrasound reflected wave reflected from one or more specimen features in the organic specimen resultant from an additional ultrasound incident wave transmitted into the organic specimen in an additional propagation region by the ultrasound transducer,
wherein positional awareness is maintained between the reference propagation region and the additional propagation region using locations of the ultrasound transducer detected by the location detection unit.

35. The method as recited in claim 34,
wherein the reference propagation region, the reference model region, and the additional propagation region are planes.

36. The method as recited in claim 34, further comprising:
identifying an additional model region in the anatomic model data corresponding to the additional propagation region using positional awareness information.

37. The method as recited in claim 36, wherein the reference propagation region, the reference model region, the additional propagation region, and the additional model region are planes.

38. The method as recited in claim 36, further comprising:
identifying at least one specimen feature in the ultrasound data of the additional propagation region and its corresponding model feature in the anatomic model data of the additional model region.

39. The method as recited in claim 36, further comprising:
creating an ultrasound image using the ultrasound data for the additional propagation region and/or
creating a model image using the anatomic model data for the additional model region.

40. The method as recited in claim 39, further comprising:
identifying at least one specimen feature in the ultrasound image of the additional propagation region and its corresponding model feature in the model image of the additional model region.

41. The method as recited in claim 39, further comprising:
issuing a command to a display module to display the ultrasound image and the model image.

42. The method as recited in claim 41, wherein the ultrasound image and the model image displayed on the display module comprise:
a static, two-dimensional ultrasound image and an associated static, two-dimensional model image, and/or
a static, three-dimensional ultrasound image and an associated static, three-dimensional model image, and/or
a set of time varying, two-dimensional ultrasound images and an associated set of time varying, two-dimensional model images, and/or
a set of time varying, three-dimensional ultrasound images and an associated set of time varying, three-dimensional model images.

43. The method as recited in claim 34, wherein the anatomic model data are obtained
from at least part of data from a representative human male or a representative human female, and/or
from at least part of data from a representative organic specimen that is other than the organic specimen from which the ultrasound data are obtained, and/or
from at least part of data from the organic specimen from which the ultrasound data are obtained, and/or
from one or more photographs and/or other images and/or other sets of data of one or more physical cross-sections of at least part of the organic specimen or a representative organic specimen.

44. The method as recited in claim 34, further comprising:
identifying a distinctive specimen feature in, and/or an aberrant feature in, and/or an instrument inserted into the organic specimen.

45. The method as recited in claim 34, wherein the anatomic model data is obtained from the Visible Human Project data for a representative human male or a representative human female.

* * * * *